United States Patent
Welch et al.

(10) Patent No.: US 10,501,575 B2
(45) Date of Patent: Dec. 10, 2019

(54) BIOMIMETIC FLUOROSCOPIC FILMS

(71) Applicant: THE BOARD OF REGENTS OF THE UNIVERSITY OF TEXAS SYSTEM, Austin, TX (US)

(72) Inventors: Tre Raymond Welch, Austin, TX (US); Amy Claire Kauffman, Austin, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 42 days.

(21) Appl. No.: 15/573,892

(22) PCT Filed: May 26, 2016

(86) PCT No.: PCT/US2016/034300
§ 371 (c)(1),
(2) Date: Nov. 14, 2017

(87) PCT Pub. No.: WO2016/191544
PCT Pub. Date: Dec. 1, 2016

(65) Prior Publication Data
US 2018/0291142 A1    Oct. 11, 2018

Related U.S. Application Data

(60) Provisional application No. 62/166,446, filed on May 26, 2015.

(51) Int. Cl.
*C08G 63/685* (2006.01)
*C08J 5/18* (2006.01)
(Continued)

(52) U.S. Cl.
CPC ........ *C08G 63/6858* (2013.01); *A61K 31/573* (2013.01); *A61K 47/6935* (2017.08);
(Continued)

(58) Field of Classification Search
CPC .......................... C08G 63/6858; C08G 63/52
See application file for complete search history.

(56) References Cited

U.S. PATENT DOCUMENTS

| 4,888,413 A | * | 12/1989 | Domb | ................ A61K 9/204 |
| | | | | 424/78.17 |
| 5,536,490 A | * | 7/1996 | Klaveness | ............ A61K 49/223 |
| | | | | 424/9.52 |

(Continued)

OTHER PUBLICATIONS

Tang et al. (Progress in Polymer Science 38 (2013) 462-502) (Year: 2013).*

(Continued)

*Primary Examiner* — Liam J Heincer
(74) *Attorney, Agent, or Firm* — Norton Rose Fulbright US LLP

(57) ABSTRACT

Disclosed are biomimetic imageable polymeric materials that include a polymer or copolymer and a covalently-linked contrasting agent where the disclosed films are both bioresorbable and visible by X-ray fluoroscopic imaging and/or magnetic resonance imaging. The invention also provides methods of preparing the polymeric materials and their use in and as implantable medical devices.

18 Claims, 21 Drawing Sheets

(51) Int. Cl.
*C08G 63/87* (2006.01)
*A61L 27/18* (2006.01)
*A61L 27/50* (2006.01)
*A61L 31/06* (2006.01)
*A61L 31/18* (2006.01)
*A61K 47/69* (2017.01)
*A61K 31/573* (2006.01)
*A61L 27/54* (2006.01)
*A61L 27/58* (2006.01)
*A61L 31/14* (2006.01)
*A61L 31/16* (2006.01)
*C08G 63/82* (2006.01)

(52) U.S. Cl.
CPC ............ *A61L 27/18* (2013.01); *A61L 27/50* (2013.01); *A61L 27/54* (2013.01); *A61L 27/58* (2013.01); *A61L 31/06* (2013.01); *A61L 31/148* (2013.01); *A61L 31/16* (2013.01); *A61L 31/18* (2013.01); *C08G 63/826* (2013.01); *C08G 63/87* (2013.01); *C08J 5/18* (2013.01); *A61L 2300/426* (2013.01); *C08J 2367/06* (2013.01)

(56) References Cited

U.S. PATENT DOCUMENTS

| | | | | |
|---|---|---|---|---|
| 5,674,468 A * | 10/1997 | Klaveness | ........... | A61K 49/1821 424/9.3 |
| 5,733,951 A * | 3/1998 | Yaszemski | ............ | A61L 24/046 424/423 |
| 5,856,415 A * | 1/1999 | Lagace | ...................... | C08F 8/42 524/399 |
| 6,361,759 B1 * | 3/2002 | Frayne | ................. | A61K 49/085 424/9.1 |
| 6,896,874 B2 * | 5/2005 | Li | ......................... | A61K 49/085 424/9.1 |
| 7,790,141 B2 * | 9/2010 | Pathak | ............... | A61K 49/0442 424/1.11 |
| 2003/0099764 A1 * | 5/2003 | Li | ......................... | A61K 49/085 427/2.24 |
| 2003/0100830 A1 * | 5/2003 | Zhong | ................... | A61L 29/145 600/431 |
| 2004/0143180 A1 * | 7/2004 | Zhong | ................ | A61K 49/1896 600/410 |
| 2005/0152842 A1 | 7/2005 | Li | ................ | 424/9.322 |
| 2006/0171895 A1 * | 8/2006 | Bucay-Couto | ............ | A61F 2/07 424/9.36 |
| 2007/0009441 A1 | 1/2007 | Erathodiyil | .................. | 424/9.34 |
| 2007/0167735 A1 | 7/2007 | Zhong | ........................... | 600/410 |
| 2008/0021313 A1 * | 1/2008 | Eidenschink | ............. | A61F 2/82 600/431 |
| 2009/0012604 A1 * | 1/2009 | Schmitz | .................. | A61L 31/10 623/1.42 |
| 2009/0317335 A1 | 12/2009 | Lin | ............. | 424/9.323 |
| 2010/0284927 A1 | 11/2010 | Lu | .................. | 424/9.2 |
| 2011/0243852 A1 * | 10/2011 | Peeters | ................... | A61L 27/50 424/9.1 |
| 2012/0190793 A1 * | 7/2012 | Halter | ................ | A61K 49/0002 525/54.2 |
| 2014/0302324 A1 * | 10/2014 | Coudane | ................ | A61L 29/085 428/402 |
| 2014/0314864 A1 * | 10/2014 | Cheng | .................. | A61K 9/5031 424/497 |
| 2015/0290344 A1 * | 10/2015 | Alexis | ................ | A61K 49/0442 424/9.451 |
| 2016/0151124 A1 * | 6/2016 | Domb | ..................... | A61L 31/06 600/414 |
| 2016/0270895 A1 * | 9/2016 | Zoll | ...................... | A61B 18/18 |

OTHER PUBLICATIONS

Search Report and Written Opinion in International Application No. PCT/US2016/034300 dated Sep. 2, 2016.

\* cited by examiner

BIOMIMETIC FLUOROSCOPIC FILMS

CROSS-REFERENCE TO RELATED APPLICATIONS

This application is a national phase application under 35 U.S.C. § 371 of International Application No. PCT/US2016/034300, filed May 26, 2016, which claims benefit to U.S. Provisional Patent Application No. 62/166,446 to Welch et. al. filed May 26, 2015; the entire contents of the foregoing application are incorporated in their entirety.

FIELD OF INVENTION

The invention generally relates to imageable polymeric compositions that are bioresorbable. In particular, the invention relates to biomimetic film that are bioresorbable and visible by X-ray fluoroscopic imaging and/or magnetic resonance imaging.

BACKGROUND

A stent is any device, which is inserted into a blood vessel or other internal duct in the body to create a passage between two hollow spaces or to expand the vessel or duct to prevent or alleviate a blockage. These devices find regular use in medicine to expand coronary, vascular, biliary, prostatic, and ureteral passageways. Traditionally, such devices are fabricated from a metal mesh and remain in the body permanently or until removed through further surgical intervention. A biodegradable and bioresorbable (bioabsorbable) stent serves the same purpose, but is manufactured from a material that dissolves and is absorbed or eliminated from the body.

Commonly employed biocompatible and biodegradable materials, such as poly(glycerol sebacate) (PGS) and poly(propylene fumarate) (PPF), are polymers used in the medical field that resorb within the body with no toxicity. Disadvantageously, these polymers are inert to medical imaging technics and cannot be viewed in a rapid and convenient fashion in vivo. Typically, a contrasting medium or agent is used to enhance the contrast of structures or fluids within the body during medical imaging. A contrasting medium or agent, however, suffer in that they only provide temporary visualization as the agent may be quickly metabolized or eliminated from the body.

SUMMARY

Solutions to the problems of non-imageable implantable medical devices have been discovered. One solution is premised in a polymeric material that can be imaged under electromagnetic radiation. The polymeric material can be formed into a film, a thin sheet or be used as a coating. In addition to being detectable through electromagnetic radiation, the polymeric material can be absorbed by the body. In a particular embodiment, the polymeric material can be a polymer having the general structure (I), be a copolymer having general structure (II), or a mixture thereof. The polymeric material can be used in implantable medical devices and visible under X-ray fluoroscopic imaging, magnetic resonance imaging, or both without the use of supplemental contrasting medium or a contrast agent. When produced as a film, the film can be highly elastic and nonlinear in tensile testing, thereby providing anisotropic properties which are biomimetic of soft tissue. In one application, the film can be used in pericardium tissue, for example, as a heart patch, a heart valve, a stent, or a grafted conduit.

In a particular aspect, there is disclosed a polymeric material having a general structure of (I):

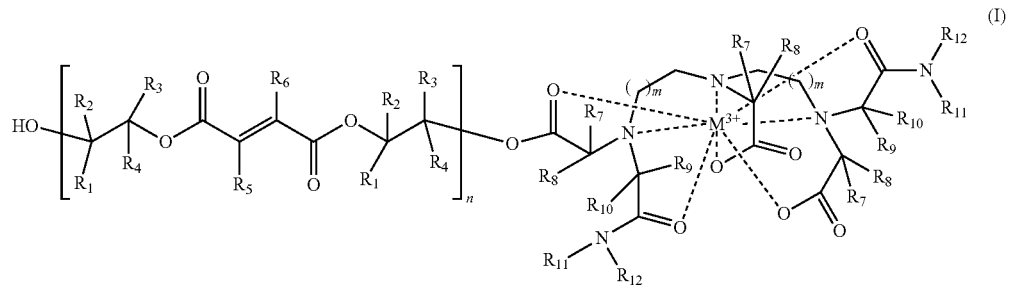

wherein $R_1$, $R_2$, $R_3$, $R_4$, $R_5$, $R_6$, $R_7$, $R_8$, $R_9$, $R_{10}$, and $R_{11}$ are each, individually, a hydrogen atom or an alkyl group; n is 1 to 4, preferably 2; m is 0 through 5, preferably 1; and M is a transition, lanthanide, or actinide ion. In one example, the polymer having general structure (I), where $R_1$ and $R_{11}$ are methyl, $R_2$, $R_3$, $R_4$, $R_5$, $R_6$, $R_7$, $R_8$, $R_9$, $R_{10}$ and $R_{12}$ are hydrogen, m is 1, and M is gadolinium and the structure is:

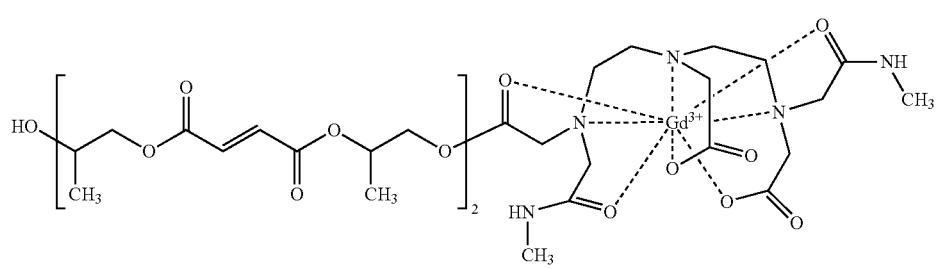

In one embodiment, there is disclosed a polymer having a general structure of (I) comprising a monomer where n is 1. The polymer has bioresorbable properties and may find application as a film or coating that emits fluorescent X-rays under electromagnetic radiation, emits electromagnetic radiation waves under an oscillating magnetic field, or both.

In another aspect there is disclosed a copolymer or blend having a general structure of (II):

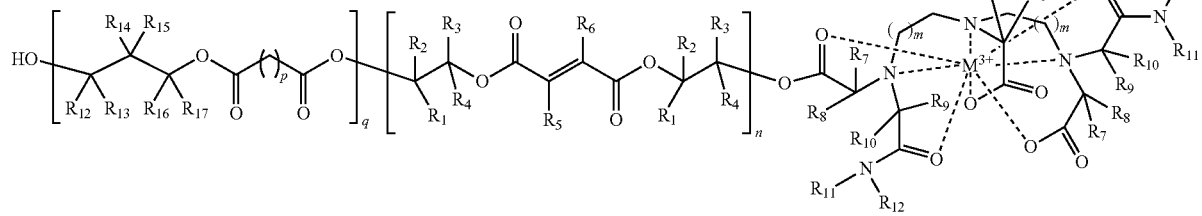

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, and $R_{17}$ are each, individually, a hydrogen atom, an alkyl group, or a hydroxyl group; p is 2 through 12; q is 1 to 3; n is 1 to 3, preferably 2; m is 0 through 5; and M is a transition, lanthanide, or actinide ion. In a one example, the copolymer having general structure (II), wherein $R_1$ and $R_{11}$ are methyl, $R_2$, $R_3$, $R_4$, $R_5$, $R_6$, $R_7$, $R_8$, $R_9$, $R_{10}$, and $R_{12}$ are hydrogen, $R_{14}$ is a free hydroxyl group or an esterified hydroxyl group, $R_{12}$, $R_{13}$, $R_{15}$, $R_{16}$, and $R_{17}$ are hydrogen, m is 1, M is gadolinium, and p is 8 structurally defined by:

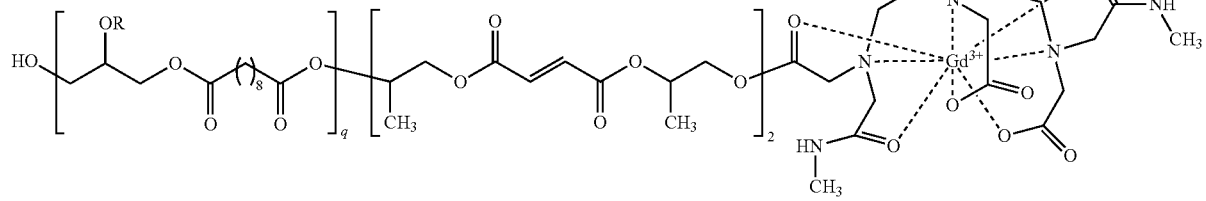

is further characterized by a Fourier transform infrared spectra with a stretches at 736 cm$^{-1}$, 1680 cm$^{-1}$, 1730 cm$^{-1}$, 3450 cm$^{-1}$, and 3512 cm$^{-1}$, wherein the 736 cm$^{-1}$ peak is attributed to the gadolinium and by H-NMR with peaks at 1.2, 1.6, 3.6, 4.2, 5.1, 5.3, 6.9 and 7.2 ppm attributable to hydrogens in the polymer matrix, and a peak at 0.9 attributable to hydrogens proximate gadolinium and methyl protons. In one embodiment, the polymer having a general structure of (II) can include a monomer where n is 1 and q is 1.

The copolymer having general structure (II) has bioresorbable properties and may find application as a film or coating that emits fluorescent X-rays under electromagnetic radiation, emits electromagnetic radiation waves under an oscillating magnetic field, or both. In certain embodiments the copolymer is attached, coupled, or coated on or in a substrate, (for example, a heart patch, a heart valve, a stent, a grafted conduit, or any combination thereof). In other embodiments, the copolymer further can also include drugs or growth factors, or both. Modification of the synthesis or surface treatment of the copolymer may provide opportunities for the incorporation of surface biomolecules, nanoparticles, microparticles, hydrophilic groups, or any combination thereof. The copolymer may have elastic properties that mimic soft tissue, for example, having an ultimate tensile strength of 600 kPa and a maximum strain of 0.65 mm/mm.

Disclosed are methods to prepare a polymer having a general structure of (I), the method can include (a) obtaining a dialkyl alkylenedioic acid, a 1,2-diol, anhydrous gadodiamide, and a Lewis acid catalyst or a Lewis base catalyst; and (b) reacting the dialkyl alkylenedioic acid, the 1,2-diol, gadodiamide and the Lewis acid catalyst or Lewis base catalyst under conditions sufficient to produce the polymer. In some embodiments, the dialkyl alkylenedioic acid and the 1,2-diol is diethyl fumarate and propylene glycol respectively, and the Lewis acid is zinc chloride or the Lewis base is ciprofloxacin. In embodiments, where ciprofloxacin is used, the ciprofloxacin can connect to the gadodiamide as shown in the structure below.

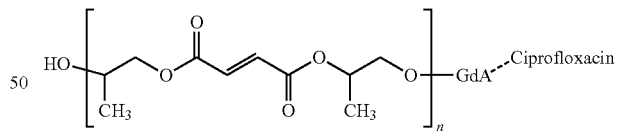

where GdA is gadodiamide and n is as defined above.

In one embodiment, a method to prepare a polymer having a general structure of (III) can include (a) obtaining a dialkyl alkylenedioic acid, a 1,2-diol, and a Lewis acid catalyst; and (b) reacting the dialkyl alkylenedioic acid, the 1,2-diol, and the Lewis acid catalyst under conditions sufficient to produce the polymer. In another embodiment, a method to prepare a polymer having a general structure of (III) can include (a) obtaining a dialkyl alkylenedioic acid, a 1,2-diol, and a Lewis base catalyst; and (b) reacting the dialkyl alkylenedioic acid, the 1,2-diol, and the Lewis base catalyst under conditions sufficient to produce the polymer. In some embodiments, the dialkyl alkylenedioic acid and the 1,2-diol of is diethyl fumarate and propylene glycol, respectively, and the Lewis base is ciprofloxacin. The reaction conditions to prepare the polymer can include a temperature of 150° C. to 200° C., preferably 170° C. to 190° C., most preferably 180° C., a pressure of 1 to 5 mmHg, preferably 1 to 2 mmHg, most preferably 1 mmHg with vigorous agitation at 200 to 300 rpm, 210 to 300 rpm, or 220 rpm. The stoichiometry of the reaction conditions to prepare the polymer in some of the disclosed methods can include a molar ratio of Lewis acid to dialkyl alkylenedioic acid of 0.0004:1 to 0.06:1, preferably 0.02:1, a molar ratio of dialkyl alkylenedioic acid to 1,2-diol of 1:2 to 1:5, preferably 1:3, and a molar ratio of gadodiamide to dialkyl alkylenedioic acid of 0.017:1 to 0.06:1, preferably 0.02:1. The stoichiometry of the reaction conditions to prepare the polymer can include a molar ratio of Lewis base to dialkyl alkylenedioic acid of 0.0004:1 to 0.06:1, preferably 0.02:1, a molar ratio of dialkyl alkylenedioic acid to 1,2-diol of 1:2 to 1:5, preferably 1:3, and a molar ratio of gadodiamide to dialkyl alkylenedioic acid of 0.017:1 to 0.06:1, preferably 0.02:1. In a non-limiting example, the reaction may be terminated when the molecular weight of the polymer is 500 Da to 1500 Da, preferably about 1000 Da.

Also disclosed are methods to prepare a copolymer having general structure (II) or (IV). Such methods can include heating a mixture of poly(1,3-diol alkanedioate) and a polymer having general structure (I) or (III) under conditions suitable to form the copolymer. In some examples the polymer and poly(1,3-diol alkanedioate) are mixed together to form a blend and the poly(1,3-diol alkanedioate) is poly(glycerol sebacate). The conditions to prepare the blend can include dissolving the poly(1,3-diol alkanedioate) and the polymer in methylene chloride; and evaporating the methylene chloride over a period of 8 to 15 hours, preferably 12 hours to form a blend. The ratio of poly(1,3-diol alkanedioate) and the polymer can be 2:1 or greater. A copolymer having general structure (II) may then be prepared, for example, by spreading the blend onto a substrate to a thickness of about 0.5 to 1 mm thick, preferably 0.8 mm, and heating the blend to a temperature of 110° C. to 140° C., 115° C. to 125° C., or 120° C. at a vacuum of 25 mmHg for 70 to 75 hours, preferably 72 hours.

In certain embodiments, a device can include a heart patch, a heart valve, a stent, a grafted conduit, a drug, or a growth factor, and the copolymer having general structure (II) or blend thereof. The device that includes the copolymer or blend thereof may be a film coated on the device, and the device may be implantable and detectable using x-ray fluoroscopic imaging, magnetic resonance imaging, or both.

In another aspect, a biomimetic fluoroscopic film can include the copolymer having general structure (II) or a blend thereof. The biomimetic film may be part of or is an implantable device and the implantable device can include a heart patch, a heart valve, a stent, a grafted conduit or any combination thereof. In some embodiments, the film can include a drug or a growth factor, surface biomolecules, nanoparticles, microparticles, hydrophilic groups, or any combination thereof.

Also disclosed are methods of imaging the polymer having general structure (I) or copolymer having general structure (II) that can include: (a) applying electromagnetic radiation, an oscillating magnetic field, or both to the polymer or copolymer; and (b) detecting the emission of fluorescent X-rays or electromagnetic radiation from the polymer or copolymer. The method can include providing the polymer or copolymer to an animal prior to step (a). In some aspects, the polymer or copolymer is adhered to a substrate. The animal can be a mammal including a human, a dog, a cat, a horse, a cow, a pig, a monkey, a rabbit, a mouse, a hamster, or a rodent. In other instances, the animal may be a fish, or a zebra fish.

In another aspect, there is disclosed a polymeric material having a general structure of (III):

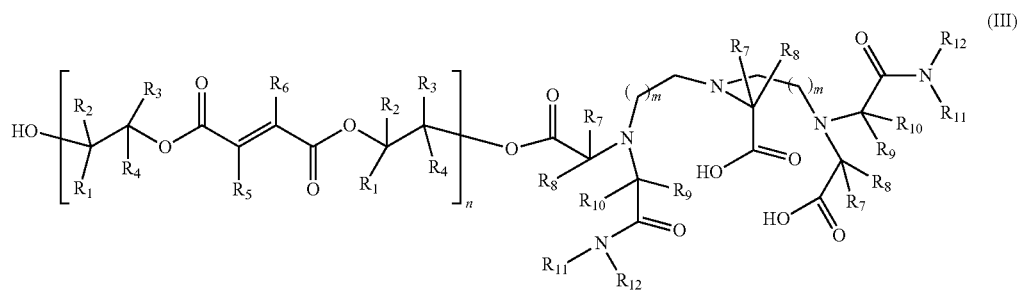

wherein $R_1$, $R_2$, $R_3$, $R_4$, $R_5$, $R_6$, $R_7$, $R_8$, $R_9$, $R_{10}$, and $R_{11}$ are each, individually, a hydrogen atom or an alkyl group; n is 1 to 4, preferably 2; and m is 0 through 5, preferably 1. In some embodiments, the polymer having general structure (III), where $R_1$ and $R_{11}$ are methyl, $R_2$, $R_3$, $R_4$, $R_5$, $R_6$, $R_7$, $R_8$, $R_9$, $R_{10}$, and $R_{12}$ are hydrogen, m is 1, n is 1, is bioresorbable and further includes a transition, lanthanide, or actinide ion.

In another aspect there is disclosed a copolymer or blend having a general structure of (IV):

wherein $R_1, R_2, R_3, R_4, R_5, R_6, R_7, R_8, R_9, R_{10}, R_{11}, R_{12}, R_{13}, R_{14}, R_{15}, R_{16},$ and $R_{17}$ are each, individually, a hydrogen atom, an alkyl group, or a hydroxyl group; p is 2 through 12; q is 1 to 3; n is 1 to 3, preferably 2; and m is 0 through 5. In a one example, the copolymer having general structure (II), wherein $R_1$ and $R_{11}$ are methyl, $R_2, R_3, R_4, R_5, R_6, R_7,$

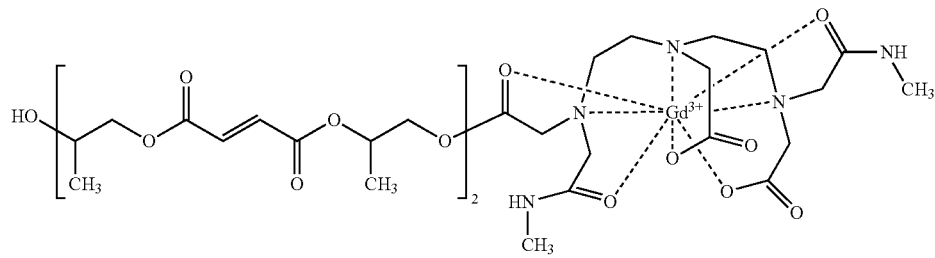

$R_8, R_9, R_{10},$ and $R_{12}$ are hydrogen, $R_{14}$ is a free hydroxyl group or an esterified hydroxyl group, $R_{12}, R_{13}, R_{15}, R_{16},$ and $R_{17}$ are hydrogen, m is 1, and p is 8.

In some embodiments, nanoparticles can be made from the compounds of the present invention (e.g., polymers, copolymers, the gadolinium containing compounds, polymers, or copolymers, the drug containing compounds, polymers, or copolymers, or combinations thereof. The nanoparticles and/or other materials containing the polymers of the invention can be used to treat mammals in need of treatments. By way of example, nanoparticles made from compounds of the present invention can be used to provide time-release drugs to treat infections, inflammation, or heart disease or the like. In a particular instance, poly(lactic-co-glycolic acid)/poly(gadodiamide fumaric acid) blend theranostic nanoparticles can be used for airway stent coatings.

In the context of the present invention, 70 embodiments are described. Embodiment 1 describes a polymer having the general structure of A polymer having a general structure of (I) shown above. Embodiments 2 is the polymer of polymer 1, wherein $R_1$ and $R_{11}$ are methyl, and $R_2, R_3, R_4, R_5, R_6, R_7, R_8, R_9, R_{10},$ and $R_{12}$ are hydrogen. Embodiment 3 is the polymer of any one of embodiments 1 through 2, wherein m is 1. Embodiment 4 is the polymer of any one of embodiments 1 through 3, wherein M is gadolinium. Embodiment 5 is the polymer of any one of claims 1 through 4, wherein n is 1. Embodiment 6 is the polymer of any one of embodiments 1 through 5, wherein the polymer is bioresorbable. Embodiment 7 is the polymer of any one of embodiments 1 through 6, wherein the polymer emits fluorescent X-rays under electromagnetic radiation, emits electromagnetic radiation waves under an oscillating magnetic field, or both. Embodiment 8 is the polymer of any one of embodiments 1 through 7, wherein the polymer is a film. Embodiment 9 is the polymer of embodiment 1, wherein the polymer is:

Embodiment 10 is a copolymer or blend thereof having a general structure of compound (II). Embodiment 11 is the copolymer of embodiment 10, wherein $R_1$ and $R_{11}$ are methyl, and $R_2, R_3, R_4, R_5, R_6, R_7, R_8, R_9, R_{10},$ and $R_{12}$ are hydrogen. Embodiment 12 is the copolymer of any one of embodiments 10 through 11, wherein m is 1. Embodiment 13 is the copolymer of any one of embodiments 10 through 12, wherein M is gadolinium. Embodiment 14 is the copolymer of any one of embodiments 10 through 13, wherein $R_{14}$ is a free hydroxyl group or an esterified hydroxyl group and $R_{12}, R_{13}, R_{15}, R_{16},$ and $R_{17}$ are hydrogen. Embodiment 15 is the copolymer of any one of embodiments 10 through 14, wherein p is 8. Embodiment 16 is the copolymer of embodiment 10, wherein the copolymer is:

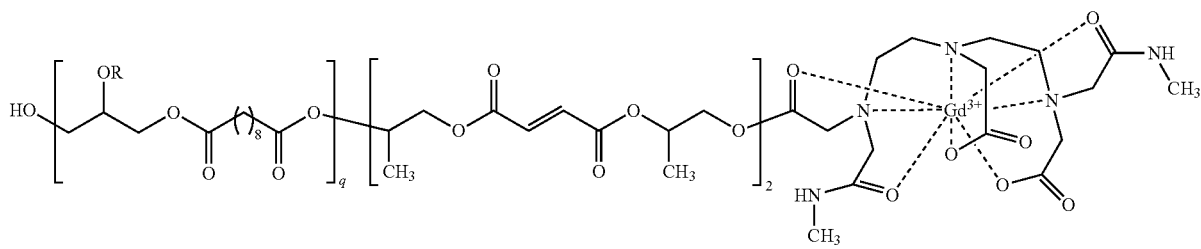

Embodiment 17 is the copolymer of any one of embodiments 10 through 16, further characterized by a Fourier transform infrared spectra with a stretches at 736 cm$^{-1}$, 1680 cm$^{-1}$, 1730 cm$^{-1}$, 3450 cm$^{-1}$, and 3512 cm$^{-1}$, wherein the 736 cm$^{-1}$ peak is attributed to the gadolinium. Embodiment 18 is the copolymer of any one of embodiments 10 through 17, further characterized by H-NMR with peaks at 1.2, 1.6, 3.6, 4.2, 5.1, 5.3, 6.9 and 7.2 ppm attributable to hydrogens in the polymer matrix, and a peak at 0.9 attributable to hydrogens proximate to gadolinium and methyl protons. Embodiment 19 is the copolymer of any one of embodiments 10 through 18, wherein the copolymer is bioresorbable. Embodiment 20 is the copolymer of any one of embodiments 10 through 19, wherein the copolymer is detectable by X-ray fluoroscopic imaging, magnetic resonance imaging, or both. Embodiment 21 is the copolymer of any one of embodiments 10 through 20, wherein the copolymer is a film. Embodiment 22 is the copolymer of any one of embodiments 10 through 21, comprising a polymer where q=1 and n=1. Embodiment 23 is the copolymer of any one of embodiments 10 through 22, wherein the copolymer is comprised on or in a substrate, wherein the substrate comprises a heart patch, a heart valve, a stent, a grafted conduit, or any combination thereof. Embodiment 24 is the copolymer of any one of embodiments 10 through 23, wherein the copolymer is film. Embodiment 25 is the copolymer of embodiment 24, wherein the film is comprised in or is a heart patch, a heart valve, a stent, or a grafted conduit, or any combination thereof. Embodiment 26 is the copolymer of any one of embodiments 10 through 25, wherein the copolymer further comprises drugs or growth factors, or both. Embodiment 27 is the copolymer of any one of embodiments 10 through 26, wherein the copolymer further comprises surface biomolecules, nanoparticles, microparticles, hydrophilic groups, or any combination thereof. Embodiment 28 is the copolymer of any one of embodiments 10 through 27, wherein the film has an ultimate tensile strength of 600 kPa and a maximum strain of 0.65 mm/mm.

Embodiment 29 describes a method to prepare the polymer of any one of embodiments 1 through 9, the method can include (a) obtaining a dialkyl alkylenedioic acid, a 1,2-diol, anhydrous gadodiamide, and a Lewis acid catalyst or Lewis base catalyst; and (b) reacting the dialkyl alkylenedioic acid, the 1,2-diol, gadodiamide and the Lewis acid catalyst or Lewis base catalyst under conditions sufficient to produce the polymer. Embodiment 30 is the method of embodiment 29, wherein the dialkyl alkylenedioic acid and the 1,2-diol of are diethyl fumarate and propylene glycol. Embodiment 31 is the method of any one of embodiments 29 through 30, wherein the Lewis acid is zinc chloride or the Lewis base is ciprofloxacin. Embodiment 32 is the method of any one of embodiments 29 through 31, wherein the conditions comprise a temperature of 150° C. to 200° C., preferably 170° C. to 190° C., most preferably 180° C., a pressure of 1 to 5 mmHg, preferably 1 to 2 mmHg, most preferably 1 mmHg with vigorous agitation. Embodiment 33 is the method of embodiment 32, wherein the vigorous agitation comprises stirring at 200 to 300 rpm, 210 to 300 rpm, or 220 rpm. Embodiment 34 is the method of any one of embodiments 29 through 33, wherein a molar ratio of Lewis acid or Lewis base to dialkyl alkylenedioic acid is 0.0004:1 to 0.06:1, preferably 0.02:1. Embodiment 35 is the method of any one of embodiments 29 through 34, wherein a molar ratio of dialkyl alkylenedioic acid to 1,2-diol is 1:2 to 1:5, preferably 1:3. Embodiment 36 is the method of any one of embodiments 29 through 35, wherein a molar ratio of gadodiamide to dialkyl alkylenedioic acid is 0.003:1 to 0.06:1, preferably 0.02:1. Embodiment 37 is the method of any one of embodiments 29 through 36, wherein the conditions further comprise terminating the reaction when the molecular weight of the polymer is 500 Da to 1500 Da, preferably about 1000 Da.

Embodiment 38 is a method to prepare the copolymer or blend thereof from any of embodiments 10 through 28, the method can include heating a mixture of poly(1,3-diol alkanedioate) and the polymer from any one of embodiments 1 to 12 under conditions suitable to form the copolymer or blend thereof. Embodiment 39 is the method of embodiment 38, wherein the poly(1,3-diol alkanedioate) is poly(glycerol sebacate). Embodiment 40 is the method of any of embodiments 38 through 39, wherein the mixture is prepared by dissolving the poly(1,3-diol alkanedioate) and the polymer in methylene chloride; and evaporating the methylene chloride over a period of 8 to 15 hours, preferably 12 hours to form a blend, wherein a ratio of poly(1,3-diol alkanedioate) and the polymer is 2:1 or greater. Embodiment 42 is the method of any of embodiments 38 through 40, further comprising spreading the blend onto a substrate to a thickness of about 0.5 to 1 mm thick, preferably 0.8 mm. Embodiment 43 is the method of any of embodiments 38 through 41, wherein the conditions comprise a temperature of 110° C. to 140° C., 115° C. to 125° C., or 120° C. at a vacuum of 25 mmHg for 70 to 75 hours, preferably 72 hours.

Embodiment 44 is a device that includes a heart patch, a heart valve, a stent, a grafted conduit, a drug, or a growth factor, and the copolymer or blend thereof from embodiments 10 through 28. Embodiment 45 is the device of embodiment 43, wherein the copolymer or blend thereof is a film coated on the device. Embodiment 46 is the device of any one of embodiments 43 through 44, wherein the device is implantable. Embodiment 46 is the device of any one of embodiments 43 through 45, wherein the device is detectable using x-ray fluoroscopic imaging, magnetic resonance imaging, or both.

Embodiment 47 is a biomimetic fluoroscopic film that includes the copolymer or blend thereof of embodiments 10 through 28. Embodiment 48 is the film of embodiment 47, wherein the film comprises a drug, or a growth factor, nanoparticles, microparticles, surface biomolecules, hydrophilic groups, or any combination thereof. Embodiment 49 is the film of embodiments 47 through 48, wherein the film is part of or is an implantable device. Embodiment 50 is the film of embodiment 49, wherein the device is a heart patch, a heart valve, a stent, a grafted conduit or any combination thereof.

Embodiment 51 is a method of imaging the polymer from any one of embodiments 1 to 9 or the copolymer from any one of embodiments 10 to 28, the method includes (a) applying electromagnetic radiation, an oscillating magnetic field, or both to the polymer or copolymer; (b) detecting the emission of fluorescent X-rays or electromagnetic radiation from the polymer or copolymer. Embodiment 52 is the method of embodiment 51, further comprising providing the polymer or copolymer to an animal prior to step (a). Embodiment 53 is the method of embodiment 52, wherein the polymer or copolymer is adhered to a substrate. Embodiment 54 is the method of any one of embodiments 51 through 52, wherein the animal is a mammal. Embodiment 55 is the method of claim 52, wherein the animal is a human. Embodiment 56 is the method of embodiment 54, wherein the mammal is a dog, cat, horse, cow, pig, monkey, rabbit, mouse, hamster, or rodent. Embodiment 57 is the method of embodiment 52, wherein the animal is a fish, or zebra fish.

Embodiment 58 is a polymer having the general structure of compound (III). Embodiment 69 is the polymer of embodiment 58, wherein $R_1$ and $R_{11}$ are methyl, and $R_2$, $R_3$, $R_4$, $R_5$, $R_6$, $R_7$, $R_8$, $R_9$, $R_{10}$ and $R_{12}$ are hydrogen. Embodiment 60 is the polymer of any one of embodiments 58 through 59, wherein m is 1. Embodiment 61 is the polymer of any one of embodiments 58 through 60, that includes a monomer where n is 1. Embodiment 62 is the polymer of any one of embodiments 58 through 61, wherein the polymer is bioresorbable. Embodiment 63 is the polymer of any one of embodiments 58 through 62, wherein the polymer further includes a transition, lanthanide, or actinide ion.

Embodiment 64 is a copolymer or blend thereof having a general structure of compound (IV). Embodiment 65 is the copolymer of claim 64, wherein $R_1$ and $R_{11}$ are methyl, and $R_2$, $R_3$, $R_4$, $R_5$, $R_6$, $R_7$, $R_8$, $R_9$, $R_{10}$, and $R_{12}$ are hydrogen. The copolymer of any one of claims 64 through 65, wherein m is 1. Embodiment 67 is the copolymer of any one of embodiments 64 through 66, wherein $R_{14}$ is a free hydroxyl group or an esterified hydroxyl group and $R_{12}$, $R_{13}$, $R_{15}$, $R_{16}$, and $R_{17}$ are hydrogen. Embodiment 68 is a method to prepare the polymer of any one of claims 58 through 63, the method that includes (a) obtaining a dialkyl alkylenedioic acid, a 1,2-diol, and a Lewis acid catalyst; and (b) reacting the dialkyl alkylenedioic acid, the 1,2-diol, and the Lewis acid catalyst or a Lewis acid base under conditions sufficient to produce the polymer. Embodiment 69 is the method of embodiment 68, wherein the dialkyl alkylenedioic acid and the 1,2-diol of are diethyl fumarate and propylene glycol. Embodiment 70 is the method of any one of embodiments 68 through 69, wherein the Lewis acid is zinc chloride or the Lewis acid base is ciprofloxacin The following includes definitions of various terms and phrases used throughout this specification.

The term "bioresorbable" also termed bioabsorbable refers to a biodegradable material that can be broken down and absorbed by the body and that does not require mechanical removal.

The term "biomimetic" refers to a material developed using inspiration from nature useful in the design of composite materials. The definition may encompass an in situ biomaterial that adheres to adjacent tissues, nurtures cell proliferation, and acts as a replacement tissue while new growth occurs in the repair of damaged tissue.

The term "alkyl" by itself or as part of another substituent refers to a saturated or unsaturated branched, straight-chain or cyclic monovalent hydrocarbon radical having the stated number of carbon atoms (i.e., $C_1$-$C_6$ means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are ($C_1$-$C_6$) alkyl.

The terms "therapeutic agent", "drug", and "pharmaceutically active substance" are used herein interchangeably. They refer to a substance, molecule, compound, agent, factor or composition effective which is biologically active in a human being or other mammal, locally and/or systemically. Drugs can for example be substances used for the treatment, prevention, diagnosis, cure or mitigation of a disease or illness, including vitamins and mineral supplements; substances which affect the structure or the function of a mammal; pro-drugs, which are substances which become biologically active or more active after they have been placed in a physiological environment; and metabolites of drugs.

The term "room temperature" is defined as 20° C. to 25° C.

An "animal" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, fish, etc. In a preferred embodiment, the subject is a human. In another embodiment, the subject is an experimental animal or animal suitable as a disease model. A subject to be treated for a tumor, cancer, or other cellular proliferative disorder can be identified by standard diagnosing techniques for the disorder.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. For example, in certain embodiments, "treating" refers to delaying the onset of, retarding or reversing the progress of, or alleviating or preventing either the disease or condition to which the term applies, or one or more symptoms of such disease or condition. Similarly, the term "effective" means adequate to accomplish a desired, expected, or intended result.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the film's ability to emit fluorescent X-rays under electromagnetic radiation, emit electromagnetic radiation waves under an oscillating magnetic field, or both.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF ILLUSTRATIVE EMBODIMENTS

Figure 1:
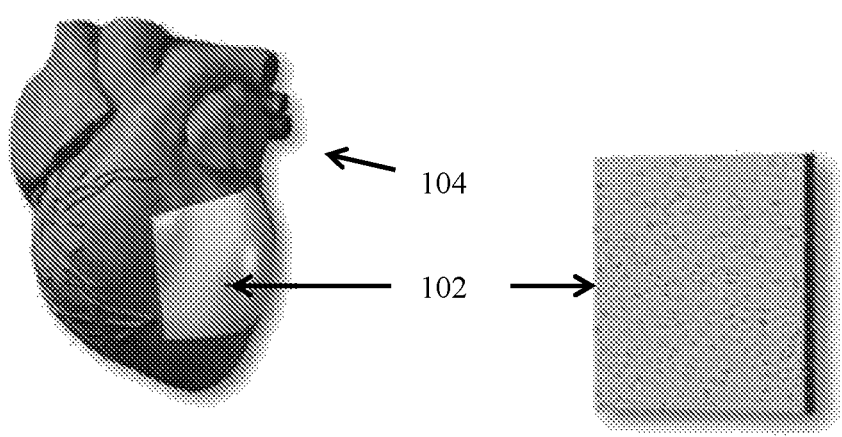
FIG. 1 is an illustration of a heart patch that includes the imageable polymeric material of the current invention alone and secured to a human heart.

Medical imaging is an important technique used to create visual representations of the interior of a body for clinical analysis and medical intervention. Typically, a contrasting medium or agent can be used to enhance the visibility of internal fluids or structures during medical imaging. Bioresorbable polymers including PPF and PGS that have many advantages for use in medical devices such as stents, are not visible by medical imaging technics. The inability to visualize an implanted bioresorbable material or device is disadvantageous, for example, the surgeon would not be able to view an implanted bioresorbable device to see if it remains correctly implanted or if the device shifts or moves during the course of resorption; both are factors, which may lead to potential unwanted complications. The material of the current invention also has the ability to be formulated into particles so an injection can be used to assess 1) biodistribution within an organ such as the liver, 2) elimination from organs such as the kidneys, and 3) permeability, for example, assessing diffusion across the blood brain barrier for traumatic brain injury.

A discovery has been made that solves the problem of using devices that are not easily imaged after implantation in the body. The solution is premised on a polymeric material having general structure (I) or a copolymer having general structure (II), or a mixture thereof that can be used in implantable medical devices and visible under X-ray fluoroscopic imaging and/or magnetic resonance imaging. The polymeric material can be provided as a film and/or sheet. When formed into a film, the film can be highly elastic and nonlinear in tensile testing, thereby providing anisotropic properties which are biomimetic of soft tissue. In one application, the polymeric material can be used in pericardium tissue, for example, as a heart patch, a heart valve, a stent (e.g., pediatric stents and adult stents), or a grafted conduit. In other applications, the polymeric material can be used as a platform for localized drug delivery. In a particular instance, the polymeric material can be used to deliver antibiotics (e.g., ciprofloxacin) or anti-inflammatory drugs (e.g., steroids, dexamethasone, or the like).

A. Imageable Polymeric Material

The compositions of the present invention can be formed into films or thin sheets or be used as a coating. In particular, polymeric material can be bioresorbable, biocompatible and biodegradable. Upon resorption of the polymeric material, the now uncoated implantable device, or parts of the uncoated implantable device remain, or, in some embodiments, the device disappears altogether.

1. Bioresorbable Polymers

The polymeric material of the invention may include homopolymers, copolymers, homopolymeric and copolymeric blends, terpolymers, quaterpolymers, or the like, and mixtures thereof that are bioresorbable. Without wishing to be bound by theory, it is believed that polymers (e.g., polyesters) made from "Kreb's cycle acids" or other materials endogenous to human metabolism are bioresorbable. Such materials include homopolymers or copolymers derived from carboxylic acids, such as those derived from alpha hydroxyl carboxylic acids and dicarboxylic acids. Non-limiting examples, of these polymers are homopolymers derived from succinic acid, fumaric acid, oxaloacetic acid, L-malic acid, D-malic acid, glycolic acid, L-lactic acid, D-lactic acid, glycerol, xylitol, sorbitol, sebacic acid, citric acid, α-ketoglutaric acid, and any combination thereof. Other bioresorbable polymers of the invention can include linear aliphatic polyesters and copolyesters, such as but not limited to, poly(caprolactone) (PCL), poly(hydroxybutyrate) (PHB), poly(3-hydroxybutyrate) (P3HB), poly-4-hydroxybutyrate (P4HB), polyhydroxyvalerate (PHV), polyhydroxyhexanoate (PHH), polyhydroxyoctanoate (PHO), poly(3-hydroxyvalerate), poly(valcrolactone), poly (tartronic acid), poly(β-malonic acid), poly(lactide-co-glycolide) (PLGA), D,L-lactide-epsilon-caprolactone, D,L-lactide-glycolide-epsilon-caprolactone, polyepsilon-caprolactone, glycolide-caprolactone, poly(glycerol sebacate) (PGS), poly(glycerol sebacate acrylate) (PGSA), poly(polyol sebacate) (PPS), poly(1,3-diamino-2-hydroxypropane-co-polyol sebacate) (APS), poly(diol-co-citrate) (PDC), poly(glycerol succinate) (PGlSu), poly(triol α-ketoglutarate) (PTK), polypropylene fumarate) (PPF), or bioresorbable derivatives thereof. Still more bioresorbable polymers include poly(ester-ether), polyorthoester (POE), polyanhydride, polycarbonate (PC), polysphazene, and poly (amino acid) polymers and copolymers thereof such as, but not limited to, poly(dioxanone) (PDX), 1,3-bis(p-carboxyphenoxy) propane (CPP), 1,4-bis(p-carboxyphenoxy) butane (CPB), poly(1,5-bis(-p-carboxyphenoxy) pentane, poly(1,6-bis(-p-carboxyphenoxy) hexane, poly(1,6-bis(-p-carboxyphenoxy) heptane, poly(tetraethyl oxide) (PTMO), poly(lactide-co-trimethylene carbonate) (PLTMC), poly(trimethylene carbonate) (PTMC), ethylglycinate polyphosphazene, poly(L-arginine), poly(L-histidine), poly(L-lysine), poly(L-gluamate), poly(L-aspartate), poly(L-serine), poly (L-threonine), poly(L-asparagine), poly(L-glutamine), poly (L-cysteine), poly(glycine), poly(L-proline), poly(L-alanine), poly(L-valine), poly(L-isoleucine), poly(L-leucine), poly(L-methionine), poly(L-phenylalanine), poly(L-tyrosine), poly(L-trytophan), or bioresorbable derivatives thereof. Some polyurethanes containing degradable diiscoyanates such as lysine diisocyanate (LDI) (2,6-diisocyanato-hexanoate) and other aliphatic diisocyanates like hexamethylene diisocyanate (HDI) and 1,4-butanediisocyanate can be used in the current embodiments.

2. Bioresorbable Plasticizer

A biocompatible plasticizer or plasticizers can be added to impart greater flexibility to the film or implantable device. Plasticizers that may be introduced during the polymerization process or during dissolution and blending of polymers, and may or may not be chemically bonded to the bioresorbable polymer chains. A nature-based plasticizer characterized by low toxicity and migration can include lower volatile substances with average molecular weights between, for example, 200 g/mol and 400 g/mol. Non-limiting example of such plasticizers include, diesters derived from dicarboxylic acids (e.g. sebacic acid, azelaic acid) or from ethylene glycol and propylene glycol, citric acid (e.g., tributylcitrate or triethylcitrate) or glycerol (e.g., triacetin or tributyrin).

3. Contrasting Agent

The polymeric material of the current invention can include a contrasting agent. A contrasting medium or agent may be used to enhance the visibility of certain tissues, abnormalities or disease processes during medical imaging. A number of substances that are paramagnetic may be used as contrasting agents for X-ray fluoroscopy, magnetic resonance imaging, or both, including iron, superparamagnetic iron oxide, superparamagnetic iron platinum, and potassium iodide. The contrasting substance can emit fluorescent X-rays under electromagnetic radiation and/or electromagnetic radiation waves under an oscillating magnetic field. Non-limiting examples of paramagnetic ions include transition, lanthanide, and actinide ions, as will be readily apparent to those skilled in the art, in view of the present disclosure. Preferable paramagnetic ions include $Cr^{3+}$, $Co^{2+}$, $Mn^{2+}$, $Ni^{2+}$, $Fe^{3+}$, $Fe^{2+}$, $La^{3+}$, $Cu^{2+}$, $Gd^{3+}$, $Ce^{3+}$, $Tb^{3+}$, $Pr^{3+}$, $Dy^{3+}$, $Nd^{3+}$, $Ho^{3+}$, $Pm^{3+}$, $Er^{3+}$, $Sm^{3+}$, $Tm^{3+}$, $Eu^{3+}$, $Yb^{3+}$ and $Lu^{3+}$. More preferably, the paramagnetic ion is $Mn^{2+}$, $Fe^{3+}$ or $Gd^{3+}$, and most preferably the paramagnetic ion is $Gd^{3+}$.

The foregoing paramagnetic ions may, if desired, be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, for example, iron sulfides and ferric salts such as ferric chloride.

These paramagnetic ions may also be more preferably bound, for example, through covalent or noncovalent association, to chelating agents, including hydrophilic derivatives thereof. These chelating agents include ligands having multiple denticity, for example, bidenate, tridentate, tertradentate, pentadentate, hexadentate, heptadentate, and octadentate for complexation with transition, lanthanide and actinide elements having varying outer valence shell orbital configurations. Preferable complexing agents include, for example, diethylenetriaminepentaacetic acid (DTPA), ethylene-diaminetetraacetic acid (EDTA), 1,4,7,10-tetraazacyclododecane-N,N',N',N'''-tetraacetic acid (DOTA), 3,6,9-triaza-12-oxa-3,6,9-tricarboxymethylene-10-carboxy-13-phenyl-tridecanoic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,1 1-tetraazacyclotetradecane-N,N',N'', N'''-tetraacetic acid (TETA), kryptands (macrocyclic complexes), and desferrioxamine. More preferably, the complexing agents are EDTA, DTPA, DOTA, and kryptands, most preferably DTPA. Other hydrophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP), N,N'-bis-(carboxy-octadecylamido-methyl-N-2,3-dihydroxypropyl)ethylenediamine-N,N'-diacetate (EDTA-ODP), N,N'-Bis(carboxy-laurylamidomethyl-N-2,3-dihydroxypropyl)ethylenediamine-N,N'-diacetate (EDTA-LDP), and the like.

In some embodiment, commercial contrasting agents containing ligands appropriate for covalent linkage to the disclosed polymers and copolymers can be used. Commercial contrasting agents include, for example, gadolinium-based gadoterate, gadodiamide, gadobenate, gadopentetate, gadoteridol, gadofosveset, gadoversetamide, gadoxetate, and gadobutrol.

4. Therapeutic Agents

The polymeric material of the present can include therapeutic agents, growth factors and/or the like. Therapeutic agents can include drug-like molecules (e.g., an antibacterial agent (antibiotic), a steroid, a corticosteroid, a hormone, an antacid, an anti-inflammatory agent, an anti-thrombotic agent, an anti-anginal agent, an antihistamine, a central nervous system agent, and an opiate), proteins, peptides, antibodies, antibody fragments, aptamers and small molecules and growth factors or any hydrophobic therapeutic agent. Non-limiting examples of a corticosteroid includes prednisolone, fluorometholone, dexamethasone, rimexolone, medrysone, physiologically acceptable salts thereof, derivatives thereof, and any combinations thereof. Non-limiting examples of antibiotics include ciprofloxacin, amoxicillin, penicillin, azithromycin, and an antimicrobial. Non-limiting examples of growth factors include osteoblast growth factors beta 1, vascular endothelial growth factor (VEGF), insulin, and the like.

5. Other Additives

The polymeric material of the present invention may also contain suitable additives. These additives can be included in the formulation at any stage of the preparation or synthesis. The desired concentrations of the additives in the formulation for conferring the intended effect, as recognized by those skilled in the art, can be assayed using conventional methods.

B. Preparation of the Polymeric Material

1. Preparation of the Imageable Polymeric Material

The contrasting agent may be incorporated in the present compositions in a variety of ways. Without wishing to be bound by theory, it is believed that the ligand of the contrast agent may be incorporated in the present compositions by being associated covalently or non-covalently with one or more of the atoms or polymers, which are included in the polymeric compositions of the present invention. As noted above, preferred polymeric materials of the present invention can include polymer, copolymer, and plasticizer compounds, or combinations thereof. In these compositions, the contrasting agents are preferably associated covalently with the polymer or copolymer compounds. Even more preferably, the contrasting agents are covalently linked to the bioresorbable polymer or copolymer at the terminus of each polymer or copolymer chain.

The amount of the contrasting agent, which may be incorporated in the present polymeric material, can vary depending, for example, on the particular polymer or copolymer involved, as well as the location and/or particular implant and/or therapeutic application. In some embodiments, the contrasting agent comprises 0.1 to 0.001 mole percent or 0.05 to 0.002 mole percent of the polymeric material. For example, the bioresorbable film contains 0.05, 0.04, 0.03, 0.02, 0.01, 0.009, 0.008, 0.007, 0.006, 0.005, 0.004, 0.003, 0.002, 0.001 mole percent of contrasting agent. In certain preferred embodiments, the polymeric material comprises 0.02 mole percent of contrasting agent.

Exemplary covalent bonds by which the ligand of the contrasting agents are associated with the bioresorbable polymer or copolymer include, for example, amide (—CONH—); thioamide (—CSNH—); ether (—O—); ester (—COO—); thioester (—COS—); carbamates; —NH—; —NR—, where R is alkyl, for example, alkyl of from 1 to about 4 carbons; urethane; and substituted imidate; and combinations of two or more of these. Covalent bonds between ligand and, for example, polymers, may be achieved through the use of molecules that may act as spacers to increase the conformational and topographical flexibility of the ligand. Non-limiting examples of such spacers include dicarboxylic acids (e.g., succinic acid, 1,6-hexanedioic acid, 1,8-octanedioic acid, and the like) and modified amino acids (e.g., 6-aminohexanoic acid, 4-aminobutanoic acid, and the like). In addition, in the case of chelating agents, which include peptide moieties, sidechain-to-sidechain crosslinking can be complemented with sidechain-to-end crosslinking and/or end-to-end crosslinking. In addition, small spacer molecules, such as dimethyl suberimidate, can be used to accomplish similar objectives. The use of agents, including those used in Schiff base-type reactions, such as glutaraldehyde, can be used. The Schiff base linkages, which may be reversible linkages, can be rendered more permanent covalent linkages via the use of reductive amination procedures. This can involve, for example, chemical reducing agents, such as lithium aluminum hydride reducing agents or their milder analogs, including lithium aluminum diisobutyl hydride (DIBAL), sodium borohydride ($NaBH_4$) or sodium cyanoborohydride ($NaBH_3CN$).

The covalent linking of the ligand of the contrasting agents to the materials in the present compositions, including the bioresorbable polymers and copolymers, may be accomplished using the methods described in the Examples and throughout the specification. In a non-limiting example, the targeting ligands may be linked to the bioresorbable polymers and copolymers via the use of coupling or activation agents. Non-limiting examples of activating agents include carbonyldiimidazole (CDI), dicyclohexylcarbodiimide (DCC), diisopropylcarbodiimide (DIC), 3-(diethoxyphosphoryloxy)-1,2,3-benzotriazin-4(3H)-one (DEPBT), benzotriazol-1-yl-oxytripyrrolidinophosphonium hexafluorophosphate (PyBOP), 2-(1H-benzotriazol-1-yl)-1,1,3,3-tetramethyluronium hexafluorophosphate (HBTU), 1-Hydroxy-7-azabenzotriazole (HOAt), 1-[bis(dimethylamino)methylene]-1H-1,2,3-triazolo[4,5-b]pyridinium 3-oxide hexafluorophosphate (HATU), methyl sulfonyl chloride, Castro's Reagent, and diphenyl phosphoryl chloride. More preferably the targeting ligands may be linked to the bioresorbable polymers and copolymers via the use of a Lewis acid. Non-limiting examples of Lewis acids include both metals and non-metals, such as mineral and organic acids, borane, boron trifluoride, trimethyl borate, trimethyl borane, sulfur dioxide, nitrous oxide, montmorillonite, copper chloride, silver chloride, gold chloride, aluminum chloride, aluminum isopropoxide, antimony chloride, zinc chloride, titanium chloride, titanium isopropoxide, yttrium chloride, chromium chloride, cobalt chloride, nickel chloride, lead chloride, tin chloride, tin stearate, tin acetate, tin 2-ethylhexanoate or lead chloride, and most preferably zinc chloride.

The covalent bonds may also involve crosslinking and network polymerization. Crosslinking preferably refers to the attachment of two chains of polymer molecules by bridges, composed of either an element, a group, or a compound, which join certain carbon atoms of the chains by covalent chemical bonds. In one example, crosslinking may occur between adjacent polymer chains comprising free alcohols, acids, esters, amines, sulfates, phosphates, carbonates, carbamates, sulfonamides, or mixtures thereof. In another example, crosslinking may occur in polypeptides, which are joined by the disulfide bonds of the cystine residue. Crosslinking also may be achieved, for example, through reaction with a cross-linking agent. Non-limiting examples of crosslinking agents include 3,3'-dithiobis(succinimidylpropionate), dimethyl suberimidate, and its variations thereof, based on hydrocarbon length, and bis-N-maleimido-1,8-octane.

The reaction conditions to prepare the polymer can include a temperature of 150° C. to 200° C., preferably 170° C. to 190° C., most preferably 180° C., a pressure of 1 to 5 mmHg (133 pascals to 667 pascals), preferably 1 to 2 mmHg, most preferably 1 mmHg with vigorous agitation at 200 to 300 rpm, 210 to 300 rpm, or 220 rpm. The stoichiometry of the reaction conditions to prepare the polymer in some of the disclosed methods can include a molar ratio of Lewis acid to dialkyl alkylenedioic acid of 0.0004:1 to 0.06:1, preferably 0.02:1, a molar ratio of dialkyl alkylenedioic acid to 1,2-diol of 1:2 to 1:5, preferably 1:3, and a molar ratio of gadodiamide to dialkyl alkylenedioic acid of 0.017:1 to 0.06:1, preferably 0.02:1. In a non-limiting example, the reaction may be terminated when the molecular weight of the polymer is 500 Da, 600 Da, 700 Da, 800 Da, 900 Da, 1000 Da, 1200 Da, 1100 Da, 1200, 1300 Da, 1400 Da, 1500 Da.

The bioresorbable polymer or copolymer covalently linked to a contrasting agent of the present invention can have asymmetric centers. Compounds of the present invention containing an asymmetrically substituted atom may be isolated in optically active or racemic forms. It is well known in the art how to prepare optically active forms, such as by resolution of materials. All chiral, diastereomeric, meso, racemic forms are within the scope of this invention, unless the specific stereochemistry or isomeric form is specifically indicated.

The obtained bioresorbable polymer or copolymer covalently linked to a contrasting agent can be purified by any suitable method and characterized by NMR, MS, FT-IR, differential scanning calorimetry (DSC), dynamic mechanical analyzer (DMA), rheometer for rheology, gel permeation chromatography (GPC), XRD, XRF, X-ray crystallography, or contact angle test by sessile drop test (See, Example 3).

2. Preparation of the Polymeric Material without Contrasting Ligand

The bioresorbable polymers and copolymers without the contrasting ligand may be prepared using synthetic organic techniques, which would be readily apparent to one of ordinary skill in the art, based on the present disclosure. In a non-limiting example, the compound having the Formula (III) can be polymerized using an activating agent, a Lewis acid (e.g., zinc chloride), or a Lewis base (e.g., ciprofloxacin) described throughout the specification. The reaction conditions to prepare the polymer can include a temperature of 150° C. to 200° C., preferably 170° C. to 190° C., most preferably 180° C., a pressure of 1 to 5 mmHg, preferably 1 to 2 mmHg, most preferably 1 mmHg with vigorous agitation at 200 to 300 rpm, 210 to 300 rpm, or 220 rpm. The stoichiometry of the reaction conditions to prepare the polymer in some of the disclosed methods can include a molar ratio of Lewis acid or Lewis base to dialkyl alkylenedioic acid of 0.0004:1 to 0.06:1, preferably 0.02:1, a molar ratio of dialkyl alkylenedioic acid to 1,2-diol of 1:2 to 1:5, preferably 1:3. In a non-limiting example, the reaction may be terminated when the molecular weight of the polymer is 500 Da, 600 Da, 700 Da, 800 Da, 900 Da, 1000 Da, 1200 Da, 1100 Da, 1200, 1300 Da, 1400 Da, 1500 Da.

The polymer of formula (III) can be cross-linked or blended with other polymers to form a copolymer or polymer blend having the general formula (IV). In non-limiting example, a copolymer having the general formula (IV) can be prepared by spreading the blend onto a substrate to a thickness of about 0.5 to 1 mm thick and heating the blend to a temperature of 110° C. to 140° C., 115° C. to 125° C., or 120° C. at a vacuum of 25 mmHg for 70 to 75 hours, preferably 72 hours.

C. Methods of Using the Polymeric Material and Imageable Polymeric Material

The polymeric material and imageable polymeric material of the present invention may be used in a variety of methods. For instance in certain embodiments, the polymeric material and/or imageable polymeric material can be applied as a film or coating on an implantable device. When the imageable polymeric material is applied, the implantable device can be visualized in vivo by X-ray fluoroscopic imaging and/or magnetic resonance imaging. The polymeric material and/or imageable polymeric film ("polymeric material") of the current invention may be bonded to an implantable device by any suitable method. In one aspect the neat polymeric material or the polymeric material dissolved in an appropriate solvent can be applied to the implantable device by dipping, spraying, rolling, or brushing. The thickness of the film layer or coating can be adjusted by varying the rate at which the polymeric material is dipped or sprayed, by varying the speed of the production line, or by adjusting the consistency and density of the solubilized film, or a combination of these approaches. The coated implant can then be dried with or without heat to remove solvent or further cured to permit adhesion. In one example, PLLA fibers can be spray coated and stiffened with the use of UV-photoinitiators. The thickness of the coating can provide a method to control the duration of resorption. The rate at which the polymeric material of the current invention resorbs can vary depending of the location of implantation, age, sex, and metabolic rate of the patient. The imageable polymeric material of can last in the body for days, weeks, months, or years, and preferably from about 6 months to about 1 year. Additionally the rate of resorption can be controlled by the substitution of the monomers and ligands employed in the polymeric material affecting pharmacokinetic parameters of esterase activity and metabolism, the molecular weight of PPF-Gd, or any other methods apparent to those skilled in the art.

In another aspect, the polymeric material may have adhesive characteristics and a glue-like texture that can, for example, permit direct application and adhesion. In another aspect, the polymeric material may be bonded with heat. This can be done in many different ways including, but not limited to, blowing hot air over the surfaces before bonding, radiant heat, such as infrared, laser, etc., contact heat transfer, such as by using a heated cylinder to roll over the surfaces. The polymeric material can also be laminated, extruded, ultrasonic welded, or cured with UV light. Bonding without the use of adhesives has many advantages, such as not requiring use of toxic materials, heat bonding does not substantially change the composition of the underlying material, cost savings on materials, low cost bonding equipment, no or little down time required from manufacturing to refill adhesive and/or no drying/curing time/apparatus required.

In another embodiment the polymeric material is part of or is the composition that makes up the implantable device. In one embodiment, the implantable device that is constructed in part or entirely by the imageable polymeric material (e.g., a bioresorbable fluoroscopic film) allows the implantable device to be visualized in vivo by X-ray fluoroscopic imaging and/or magnetic resonance imaging. The implanted device that is constructed from the polymeric material of the current invention can be formed by injection molding, blow molding, thermoforming, transfer molding, compression molding, extrusion, or combinations thereof. The constructed polymeric implantable device can be further cut, trimmed, stretched, twisted, or bent to desired shape. Non-limiting examples of polymeric implantable devices include a heart patch, a heart valve, a stent, or a grafted conduit as shown in FIGS. 1-4. In a particular embodiment, the polymeric implantable device is a biomimetic fluoroscopic implantable device.

Referring to FIG. 1, an illustration of the imageable polymeric material used with a human heart is described. In FIG. 1, polymeric material 102 can be obtained by the methods described throughout this specification. The imageable polymeric material 102 can be applied to the heart 104 as a patch using known methods in the art. The patch may be permanent and coated with the film or temporary and made from the film. In some embodiments, the polymeric material includes a therapeutic agent (e.g., ciprofloxacin).

Figure 2:
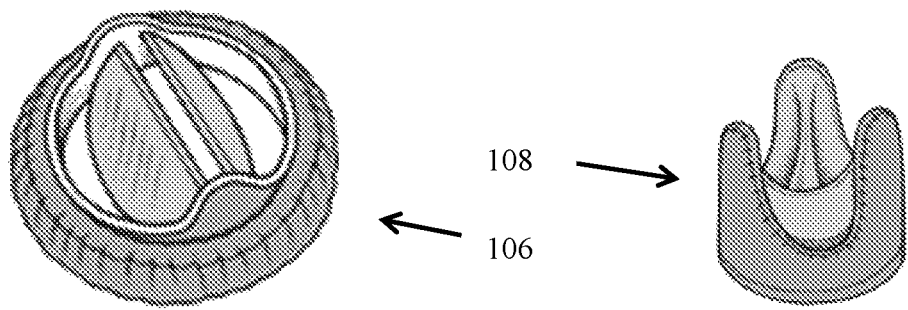
FIG. 2 is an illustration of heart valves that include the imageable polymeric material of the current invention.

Referring to FIG. 2, an illustration of the imageable polymeric material used with a heart valve is described. In FIG. 2, any part of mechanical valve 106 or bioprosthetic value 108 can contain the imageable polymeric material obtained by the methods described throughout this specification as a coating or as part of the construct where resorption would not affect function.

Figure 3:
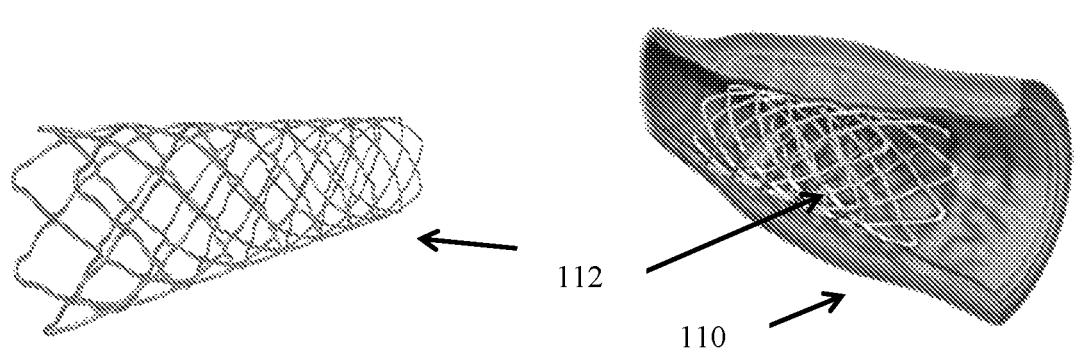
FIG. 3 is an illustration of a stent and a stent secured within an arteriosclerotic artery that includes the imageable polymeric material of the current invention.

Referring to FIG. 3, an illustration of the imageable polymeric material used with a stent is described. In FIG. 3, the polymeric material can be obtained by the methods described throughout this specification. Any part of stent 112 can contain the imageable polymeric material as a coating or as part of the construct where resorption would not affect function. Stent 112 containing imageable polymeric material can be secured within arteriosclerotic artery 110 using known methods in the art.

Figure 4:
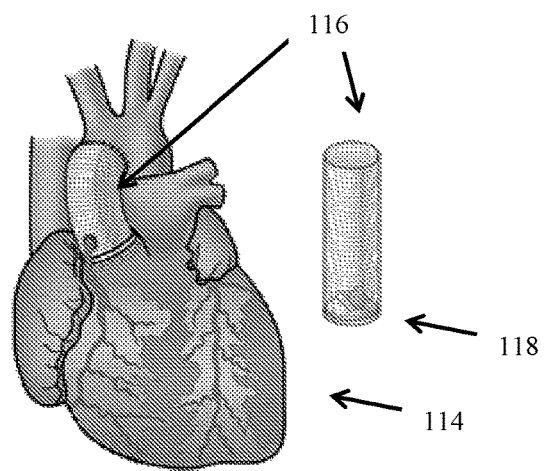
FIG. 4 is an illustration of a graft conduit that includes the imageable polymeric material of the current invention replacing the aortic arch of a human heart.

Referring to FIG. 4, an illustration of the imageable polymeric material used with a graft conduit is described. In FIG. 4, the polymeric material can be obtained by the methods described throughout this specification. Any part of graft conduit 116 may contain the film as a coating or as part of the construct where resorption would not affect function. Graft conduit 116 containing imageable polymeric material and mechanical valve 118 can be applied to human heart 114 using known methods in the art.

In another embodiment, the bioresorbable fluoroscopic implantable device may also be prepared by a 3D printing method such as selective melt sintering (SMS), selective laser sintering (SLS), fused deposition modeling (FDM), or fused filament fabrication (FFF). Additional 3D methods using liquid film formulations include stereolithography (SLA), digital light processing (DLP), or laminated object manufacturing (LOM). Photopolymerization techniques, such as in stereolithography (SLA) could be utilized where the curable photopolymer or crosslinker is also biodegradable.

The polymeric material of the current invention is flexible and elastomeric. In one embodiment, the polymeric material without a contrast agent has a nonlinear stress-strain response with an ultimate tensile strength of 366 kPa and a maximum strain of 0.47 mm/mm. In another embodiment, the imageable film has a nonlinear stress-strain response with an ultimate tensile strength of 600 kPa and a maximum strain of 0.65 mm/mm. The Young's Modulus varies with increasing strain. This type of material is represented by strain energy function, w, such as Mooney-Rivlin parameters to curve fit the data with the equations shown below. Examples of the material constant for C10=317 kPa and C01=−284 kPa for a film with a contrast agent and C10=514 kPa and C01=−4904 kPa with I1 and I2 as the strain invariants written in principal stretch directions, $\lambda 1$, $\lambda 2$, $\lambda 3$.

$$w = C_{10}(I_1 - 3) + C_{01}(I_2 - 3)$$

$$I_1 = \lambda_1^2 + \lambda_2^2 + \lambda_3^2 = \frac{2}{\lambda_3} + \lambda_3^2$$

$$I_2 = \lambda_1^2\lambda_2^2 + \lambda_2^2\lambda_3^2 + \lambda_3^2\lambda_1^2 = \frac{1}{\lambda_3^2} + 2$$

$$I_3 = \lambda_1^2\lambda_2^2\lambda_3^2 = 1$$

In another embodiment, the polymeric material can be biomimetic with adhesive properties that adheres to adjacent tissues, nurtures cell proliferation, and acts as a replacement tissue while new growth occurs in the repair of damaged tissue. The polymeric material may find use in biomedical applications that target soft tissue replacement and the engineering of soft tissues. Non-limiting examples of soft tissue include cardiac muscle, blood, nerve, cartilage and retina. The bioresorbable fluoroscopic film may also find use in biomedical applications that target hard tissue replacement, such as for example, bone regeneration. The design and fabrication techniques in the current embodiments can also be suited to prepare devices for applications that mimic native physiological conditions. Designs may range from accordion-like honeycomb structures for cardiac patches, gecko-like surfaces for tissue adhesives to nanofibers for extra cellular matrix (ECM) like constructs, or the repair of tissues and organs.

The bioresorbable polymeric material of the present invention can be used for delivery of therapeutic agents (e.g., drug and growth factor). The ability to include therapeutic agents in or on the surface of a bioresorbable fluoroscopic film can provide to a subject advanced treatment, prevention, diagnosis, cure or mitigation of a disease or illness.

In another embodiment, the bioresorbable polymeric material of the present invention can be surface treated. Generally, hydrophilic functionalities are attached to the polymer surface, rendering it easier to wet and provides opportunities for chemical bonding. Non-limiting examples of methods to functionalize a polymer surface include plasma etching, corona treatment, chemical vapor deposition, or any combination thereof. Alternatively, the surface modification of the polymeric material of the present invention can permit the attachment of biomolecules and other hydrophilic groups that are important in cell recognition and signaling. Non-limiting examples of biomolecules and hydrophilic groups include polyethylene glycol (PEG), polyvinyl alcohol (PVA), albumin (BSA), poly(N-isopropylacrylamide) (PNIPA), polyethylene oxide (PEO), poly(acrylic acid), and the like.

In still another embodiment, the bioresorbable polymeric material of the present invention can be formulated into microparticles or nanoparticles and injected into the patient to asses biodistribution within an organ such as the liver, elimination from organs such as the kidneys, and permeability, for example, assessing diffusion across the blood brain barrier during traumatic brain injury. In some embodiments, the nano- or microparticles are used to deliver a therapeutic agent to a targeted area (e.g., a pediatric heart or lung).

D. Kits

Kits are also contemplated as being used in certain aspects of the invention. For instance, a film of the present invention can be included in a kit. A kit can include a container. Containers can include a jar, case, sachet, pouch, dispenser, package, compartment or other containers into which the films are retained. The kit can include indicia on its surface. The indicia, for example, can be a word, a phrase, an abbreviation, a picture, or a symbol.

The containers can store or dispense a pre-determined size or amount of the polymeric material or (e.g., a patch made from the polymeric material or from the imageable polymeric material), or a roll of the polymeric material (e.g., a roll of polymeric film or imageable polymeric film). The containers can contain one individually wrapped film or several layers of the film. A kit can also include instructions for using the kit and/or compositions.

Further, the films of the present invention may also be sterile, and the kits containing such films can be used to preserve the sterility. The films may be sterilized via an aseptic manufacturing process or sterilized after packaging by methods known in the art.

EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

PGS Synthesis

Figure 5:
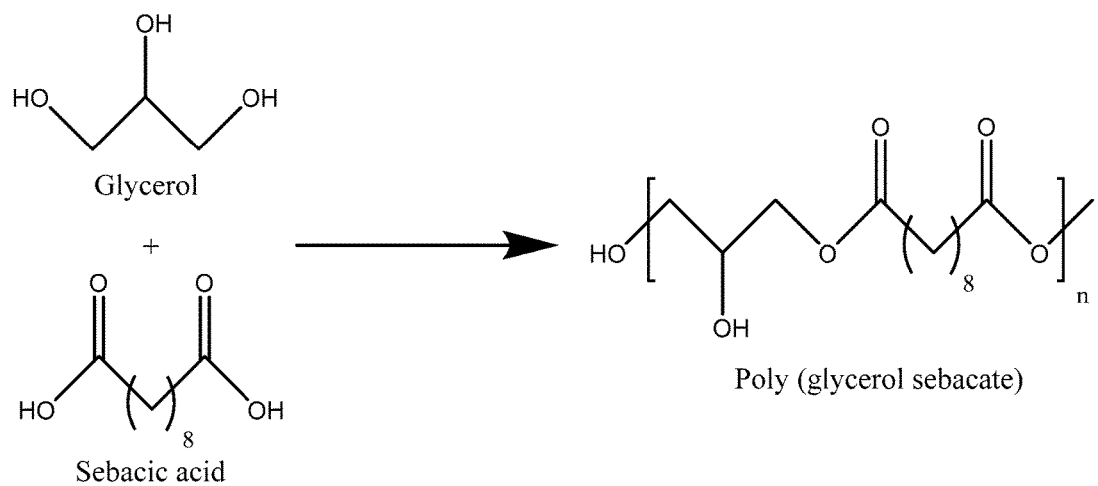
FIG. 5 is a schematic illustration showing the synthesis of poly(glycerol sebacate) (PGS).

PGS was synthesized by polycondensation. FIG. 5 depicts the reaction scheme for the polycondensation reaction. Glycerol (11 mL, 0.09 mol) and sebacic acid (23 mL, 0.16 mol) were stirred together in a 250 mL 3-neck flask at 130° C. under argon for 5 hours. The mixture was then placed under reduced pressure (40 mTorr) and heating was continued at 130° C. for 48 hours. The mixture was then cooled to 80° C. under argon for 1 hour and then poured into a storage vial at room temperature to afford the titled compound as a colorless polymer, which was used without further purification.

Example 2

PPF-Gd, PPF, PCFA, PGCFA and PGSF Synthesis

Figure 6:
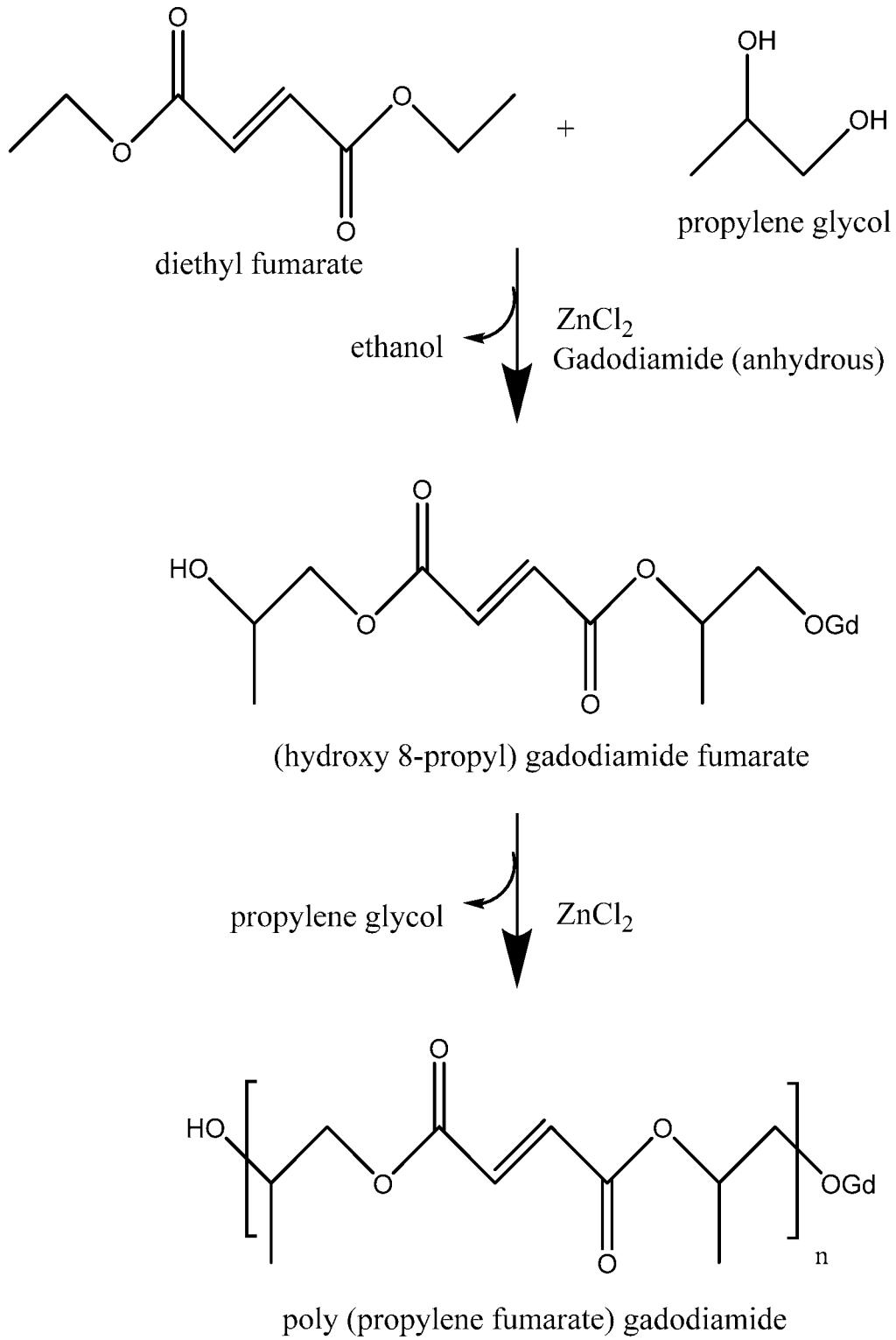
FIG. 6 is a schematic illustration showing the synthesis of poly(propylene fumarate) gadodiamide (PPF-Gd).

PPF-Gd. PFA-Gd was synthesized in a two-step transesterification process as shown in FIG. 6. A mixture of diethyl fumarate (49 mL, 0.34 mol) and propylene glycol (77.6 mL, 1.02 mol) was heated to 180° C. with stirring (220 rpm) under a nitrogen atmosphere. Dehydrated gadodiamide (1.9 mg, 0.003 mol) was then added to the mixture, the mixture was placed under reduced pressure (1 mmHg), and then heated at 180° C. The reaction was terminated when the desired molecular weight of product was obtained (1000 Da) and confirmed by gel permeation chromatography (GPC). The mixture was then cooled to room temperature to afford the PPF-Gd as an amber polymer, which was used without further purification.

PPF. PPF was synthesized in a similar manner as PPF-Gd. A mixture of Diethyl fumarate (49 mL, 0.34 mol) and propylene glycol (77.6 mL, 1.02 mol) was heated to 180° C. with stirring (220 rpm) under an argon gas purge. Zinc chloride (0.46 g, 3.0×10-3 mol) was added to the mixture, the mixture was agitated until to the zinc chloride dissolved, and the resulting mixture was heated at 180° C. The reaction was allowed to continue until 90% of theoretical yield of ethanol (24 mL) was collected in the receiving flask. Argon gas purge was then stopped and the system was placed under reduced pressure (1 mmHg). The reaction was terminated when the desired molecular weight of product was obtained (1000 Da) and confirmed by gel permeation chromatography (GPC). The mixture was then cooled to room temperature to afford the PPF compound as an amber polymer.

The amber PPF polymer was further purified. The PPF polymer was dissolved in 100 mL of dichloromethane (DCM), and a hydrogen chloride (HCL) solution (200 mL of 5% vol/vol) was added to the PPF polymer/DCM solution. The solution was repeatedly agitated and settled until no gas evolved from the solution. Upon settling the solution separated into a clear aqueous phase and cloudy amber polymer solution. The cloudy amber phase was collected and aqueous phase was discarded. The HCL wash procedure was repeated twice using deionized water in place of 5% HCL solution. With each subsequent wash, the aqueous phase appeared turbid. The wash procedure was then repeated twice with to 26% sodium chloride solution. Sodium sulfate (1 g) was added to the washed collected polymer solution and the solution was stirred at 100 rpm with for 30 minutes, and then vacuum filtered. The filtered polymer solution was then heated with stirring at 60 rpm and 80° C. overnight to remove the DCM. Final purified amber polymer solution was transferred to a storage vessel and stored at 4° C.

PCFA. PCFA was synthesized in a two-step transesterification process similar to the PPF synthesis above. A mixture of diethyl fumarate (49 mL, 0.34 mol) and propylene glycol (77.6 mL, 1.02 mol) was heated to 180° C. with stirring (220 rpm) under a nitrogen atmosphere. Ciprofloxacin (1.0 mg, 0.003 mol) was added to the mixture, the mixture was placed under reduced pressure (1 mmHg), and then heated at 180° C. The reaction was terminated when the desired molecular weight of product (1000 Da) was obtained and confirmed by gel permeation chromatography (GPC). The mixture was then cooled to room temperature to afford the PCFA as an amber polymer, which was used without further purification.

PGCFA. PGCFA was synthesized in a two-step transesterification process similar as stated above. A mixture of diethyl fumarate (49 mL, 0.34 mol) and propylene glycol (77.6 mL, 1.02 mol) was heated to 180° C. with stirring (220 rpm) under a nitrogen atmosphere. Equimolar amounts of ciprofloxacin (1.0 mg, 0.003 mol) and dehydrated gadodiamide (1.9 mg, 0.003 mol) was added to the mixture, the mixture was placed under reduced pressure (1 mmHg), and then heated at 180° C. The reaction was terminated when the desired molecular weight of product (1000 Da) was obtained and confirmed by gel permeation chromatography (GPC). The mixture was then cooled to room temperature to afford the PGCFA as an amber polymer, which was used without further purification.

Figure 7:
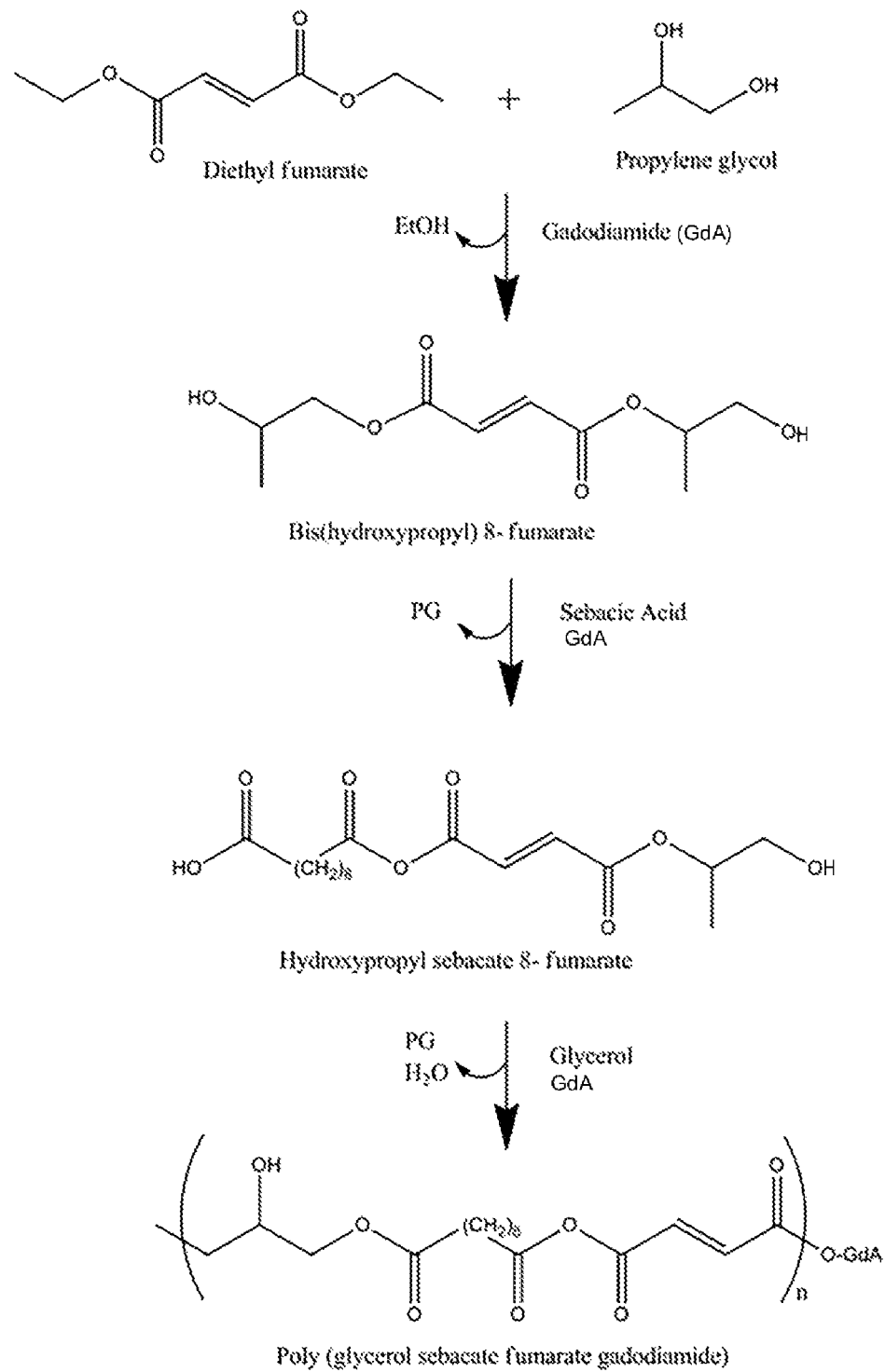
FIG. 7 is a schematic illustration showing the synthesis of poly(glycerol sebacate fumarate gadodiamide) of the present invention.

Poly(glycerol sebacate fumarate gadodiamide) (PGSF). PGSF was synthesized in a two-step transesterification as shown in FIG. 7. A mixture of diethyl fumarate (49 mL, 0.34 mol) and propylene glycol (77.6 mL, 1.02 mol) was heated to 180° C. with stirring (220 rpm) under a nitrogen atmosphere. Dehydrated gadodiamide (1.9 mg, 0.003 mol) and sebacic acid (66 g, 0.32 mol) were added to the mixture. The mixture was heated 180° C. until 90% of theoretical yield of ethanol (24 mL) was collected via distillation from the mixture. Glycerol (22 mL, 0.30 mol) was added to the mixture, the mixture was placed under reduced pressure (1 mmHg), and then heated at 180° C. The reaction was terminated when the desired molecular weight (less than 1000 Da) of product was obtained and confirmed by gel permeation chromatography (GPC). The mixture was cooled to room temperature to afford the PGSF as an amber polymer, which was used without further purification.

Example 3

PGS-PPF-Gd and PGS-PPF, Synthesis

Figure 8:
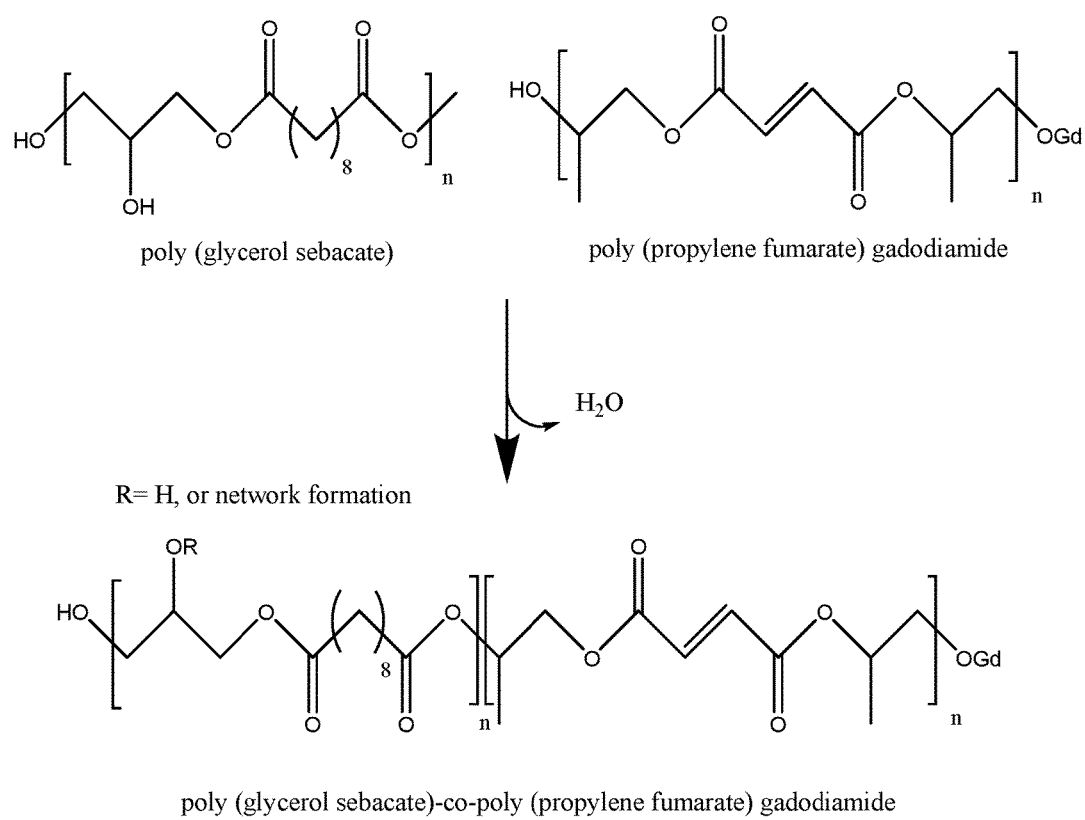
FIG. 8 is a schematic illustration showing the synthesis of poly(glycerol sebacate)-co-poly(propylene fumarate) gadodiamide (PGS-PPF-Gd) film of the present invention.

PGS-PPF-Gd. PGS-PPF-Gd was synthesized as shown in FIG. 8. A mixture of PFA-Gd (250 mg, 0.208 mmol) and PGS (500 mg, 0.454 mmol) was heated to 80° C. with stirring at 60 rpm until the mixture became homogenous. The resulting warm mixture was then spread over a glass plate with a knife to a thickness of 0.8 mm and dried in a vacuum oven for 48 hours at 120° C. The mixture was then cooled to room temperature to afford PGS-PPF-Gd as an amber film. Any non-crosslinked material remaining on the surface can be removed by washing the film with THF or DCM.

PGS-PPF. PGS-PPF was synthesized using the procedure for PGS-PPF-Gd. A mixture of PFA (0.208 mmol) and PGS (0.454 mmol) was heated to 80° C. with stirring at 60 rpm until the mixture became homogenous. The resulting warm mixture was then spread over a glass plate with a knife to a thickness of 0.8 mm and dried in a vacuum oven for 48 hours at 120° C. The mixture was then cooled to room temperature to afford the PGS-PPF as an amber film. Any non-crosslinked material remaining on the surface can be removed by washing the film with THF or DCM.

Example 4

Characterization of Polymers

Figures 9A, 9B:
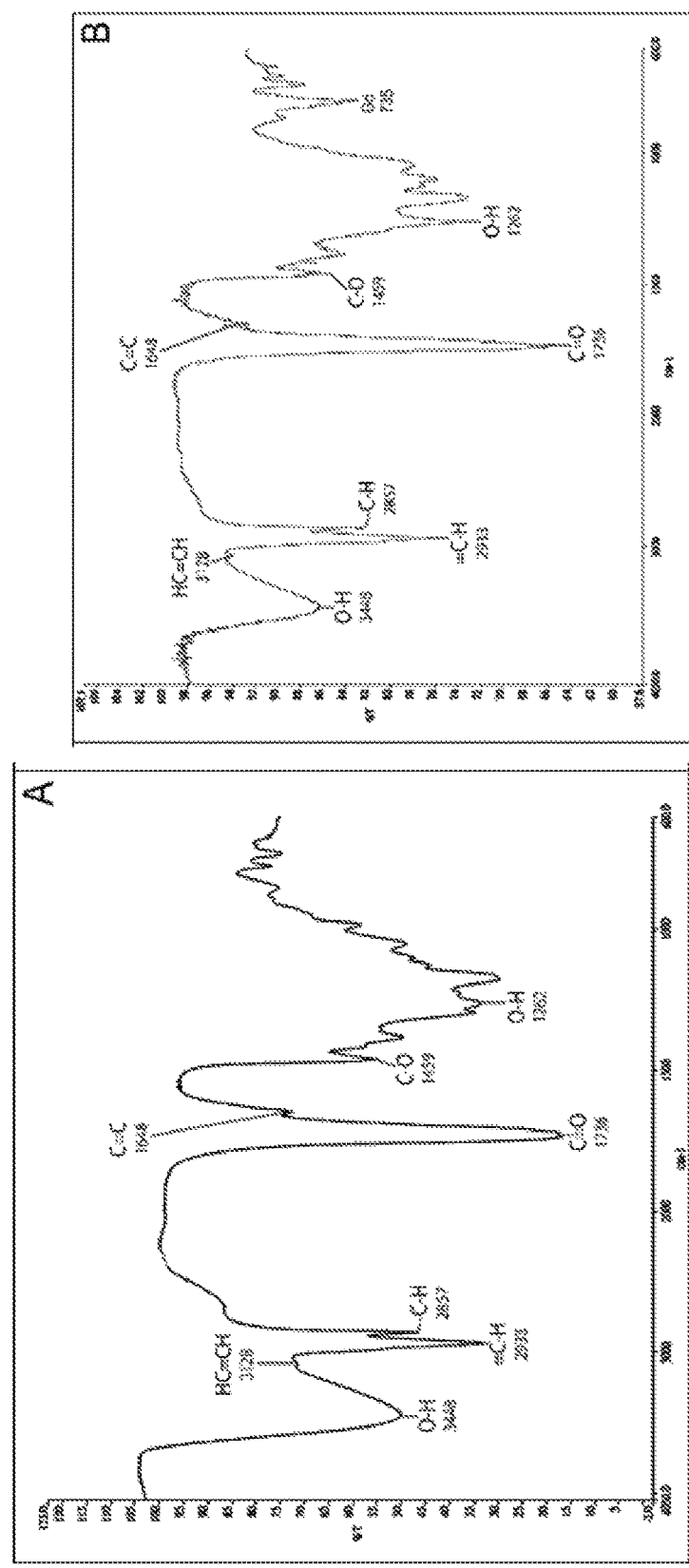
FIG. 9A is a Fourier transform infrared (FTIR) spectrum of a PGS-PPF film of the present invention.
FIG. 9B is a FTIR spectrum of a PGS-PPF-Gd film of the present invention.
Figure 9D:
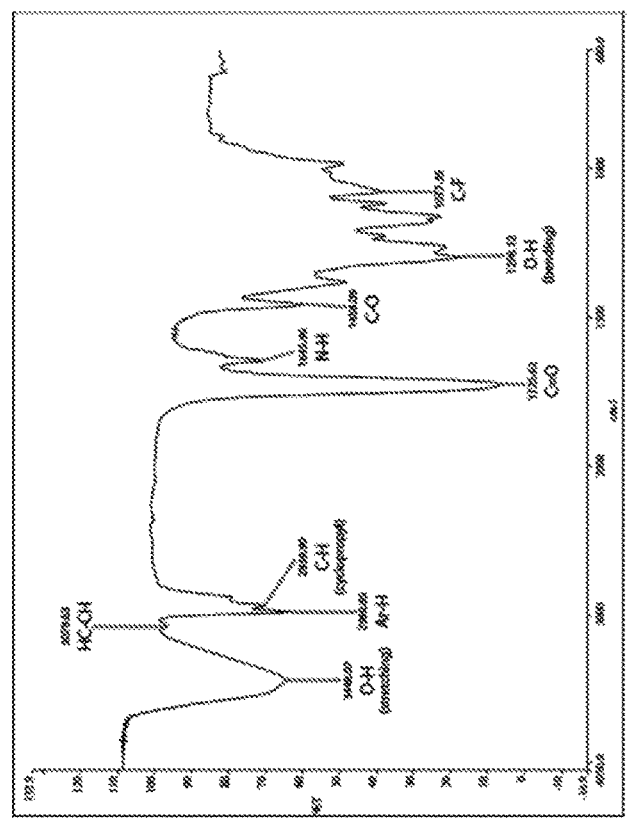
FIG. 9D is a the FTIR spectrum of a poly(ciprofloxacin fumaric acid) (PCFA) film of the present invention.
Figure 9C:
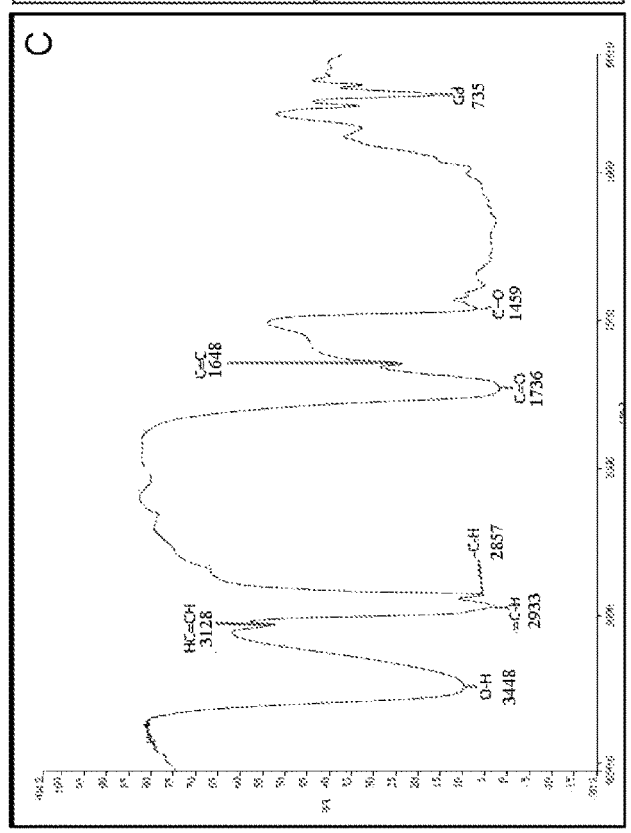
FIG. 9C is a the FTIR spectrum of a PGSF film of the present invention.
Figure 9E:
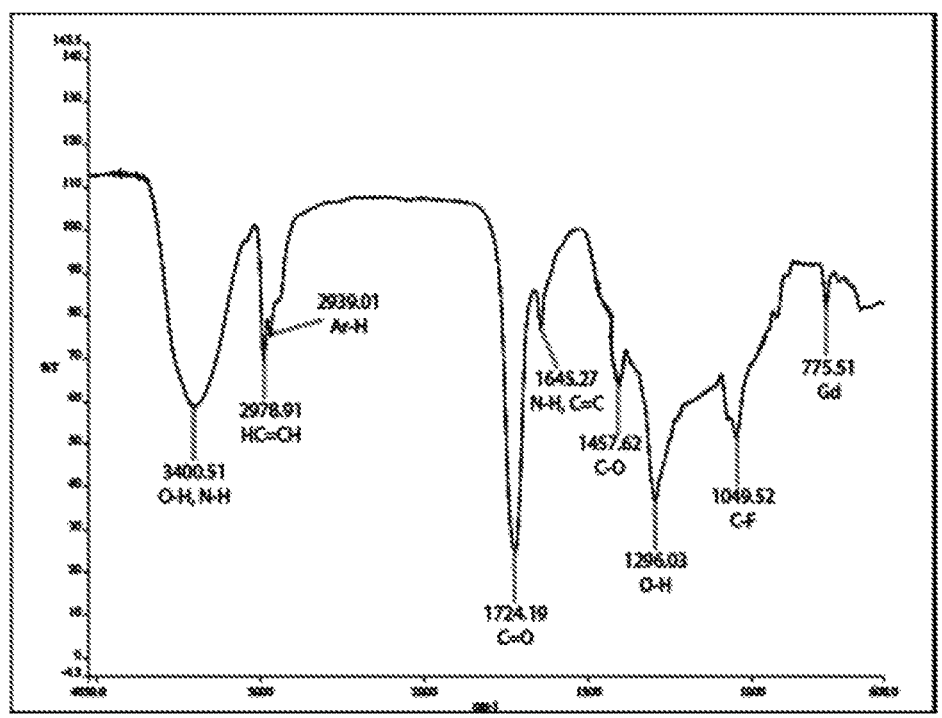
FIG. 9E is a the FTIR spectrum of a poly(gadolinium ciprofloxacin fumaric acid) (PGCFA) film of the present invention.

FTIR analysis. FTIR analyses of the polymers were conducted using a FTIR Perkin Elmer 1000 FTIR Spectrophotometer. A NaCl crystal was cleaned with methylene chloride (DCM) solvent and used as a background control for initialization of the spectrophotometer. Film samples of PGS-PPF-Gd, PGSF were dissolved in of DCM (1-2 mL) in separate vials; and prepolymer samples of PCFA, and PGCFA were dissolved in of DCM (1-2 mL) in separate vials. Drops of solution were placed on the NaCl crystal, dried and run. FIG. 9A shows the FTIR spectrum of the PGS-PPF copolymer; FIG. 9B and Table 1 shows the FTIR spectrum and labeled peaks for PGS-PPF-Gd; FIG. 9C and Table 1 show the FTIR spectrum and labeled peaks for PGSF; and PCFA and PGCFA are shown in FIG. 9D and FIG. 9E, respectively, with peaks listed in Table 2.

TABLE 1

| Peak Frequency (cm$^{-1}$) | Bond |
|---|---|
| 735 | Gadolinium |
| 1262 | O—H |
| 1459 | C—O |
| 1648 | C═C |
| 1736 | C═O |
| 2857 | —C—H |
| 2993 | ═C—H |
| 3448 | O—H |
| 3512 | N—H |

TABLE 2

| Peak Frequency (cm$^{-1}$) | Bond |
|---|---|
| 776 | Gadolinium |
| 1055 | C—F |
| 1077 | C—F |
| 1296 | O—H |
| 1458 | C—O |
| 1645 | C═C, N—H |
| 1725 | C═O |
| 2980 | Ar—H |
| 2993 | ═C—H |
| 3079 | —C—H |
| 3400 | N—H |
| 3448 | O—H |

Figure 10A:
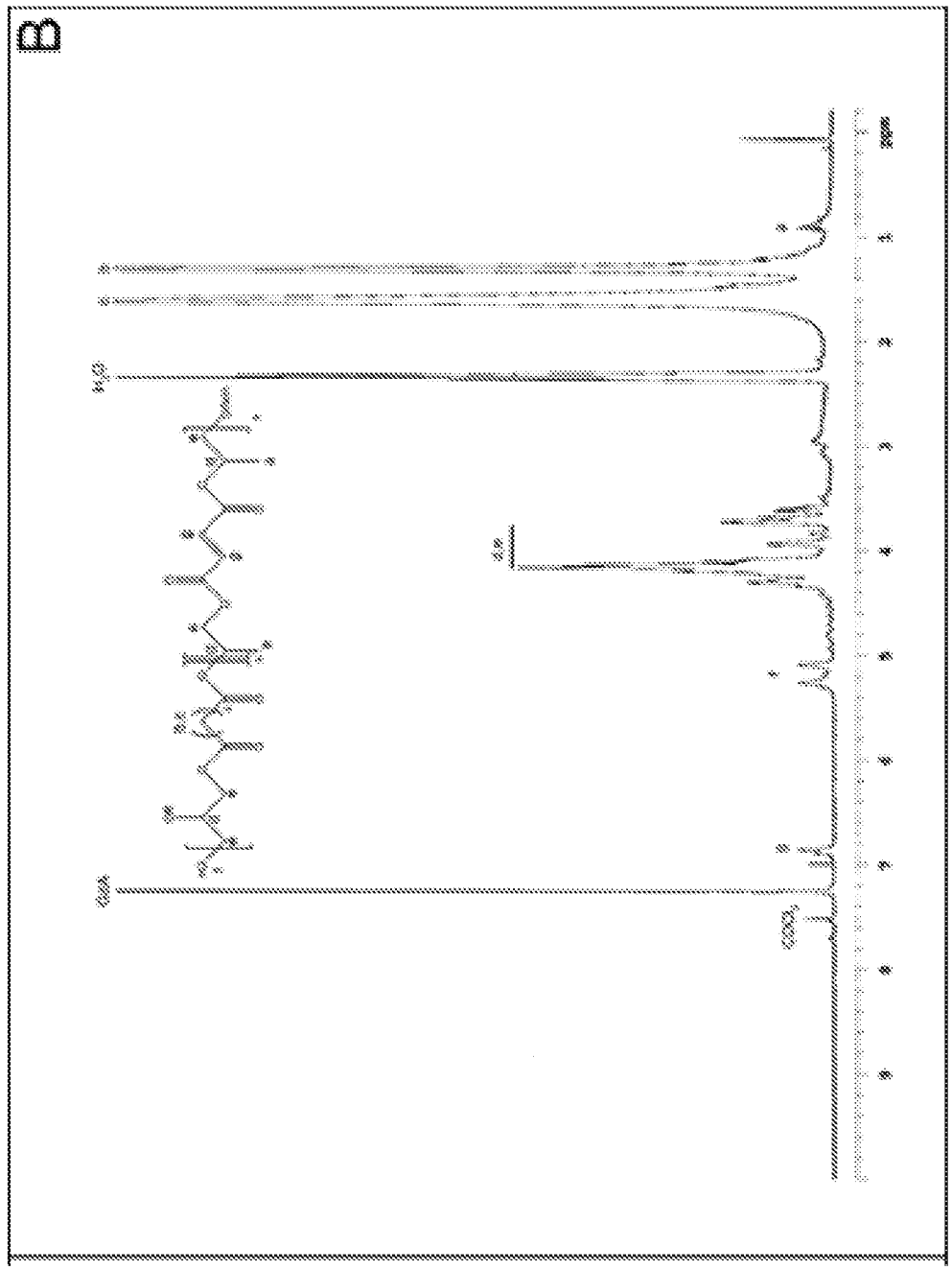
FIGS. 10A and 10B show proton nuclear magnetic resonance (H-NMR) spectra of a PGS-PPF PGS-PPF-Gd (FIG. 10A) and PGSF (FIG. 10B).
Figure 10B:
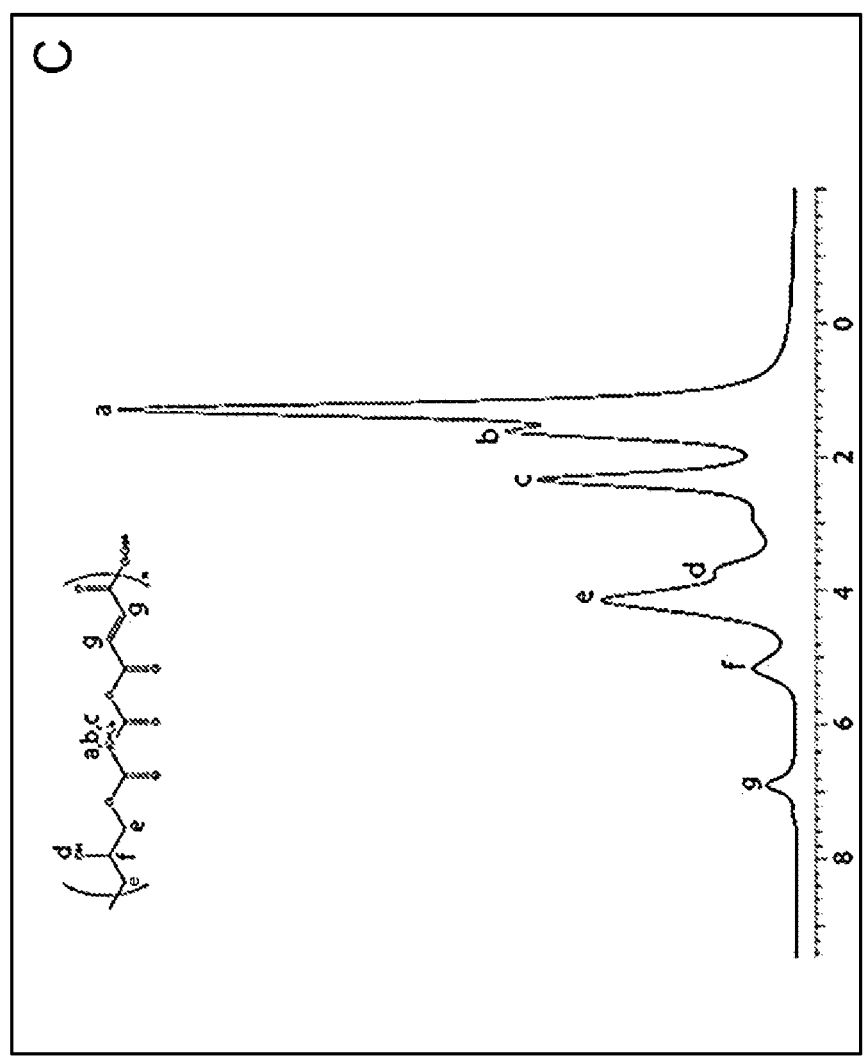

H-NMR analysis. H-NMR analyses were conducted on samples dissolved in CDCl$_3$ using a Varian Unity Inova AS600 MHz. The H-NMR spectrums for PGS-PPF-Gd and PGSF, are shown in FIG. 10A and FIG. 10B, respectively. In FIG. 10B, the PGS polymer matrix was identified at 1.2, 1.6, 2.3, 4.2 and 5.2 ppm by hydrogens located on the species labeled "a"-"f". The PPF-Gd polymer was identified at 0.9 and 6.9 ppm by additional hydrogens located on the carbons labeled "a", "d", "e", and "g". In FIG. 10B, the PGS polymer matrix was identified at 1.3, 1.6, 2.3, 3.7, 4.1, 5.1 ppm by hydrogens located at species labeled "a"-"f" and fumarate at 6.8 identified by hydrogen species labeled "g".

Figure 11A:
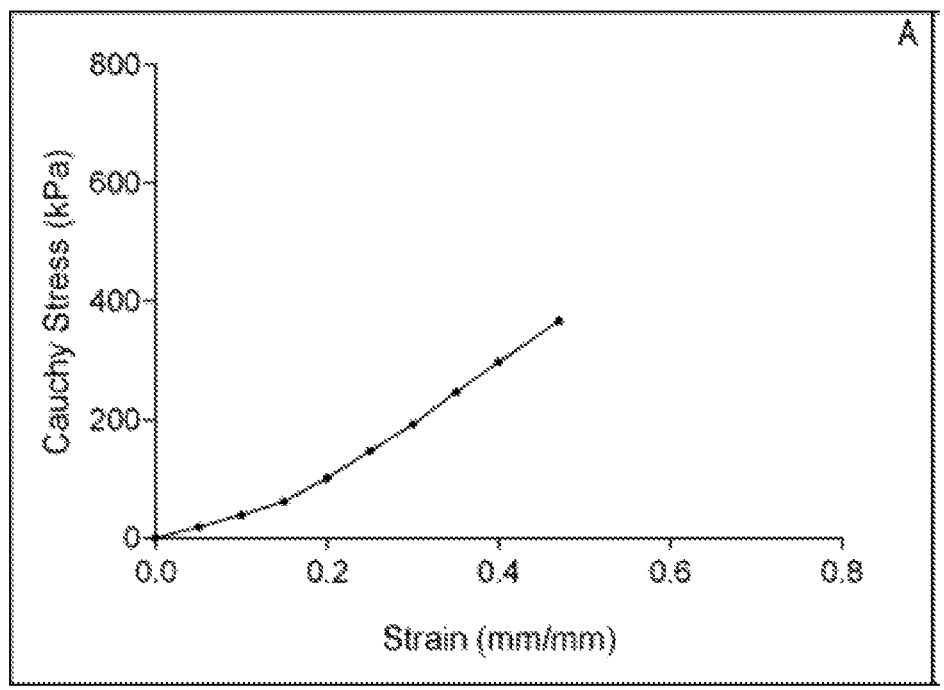
FIG. 11A is a graphical representation of the stress-strain response of PGS-PPF film.
Figure 11B:
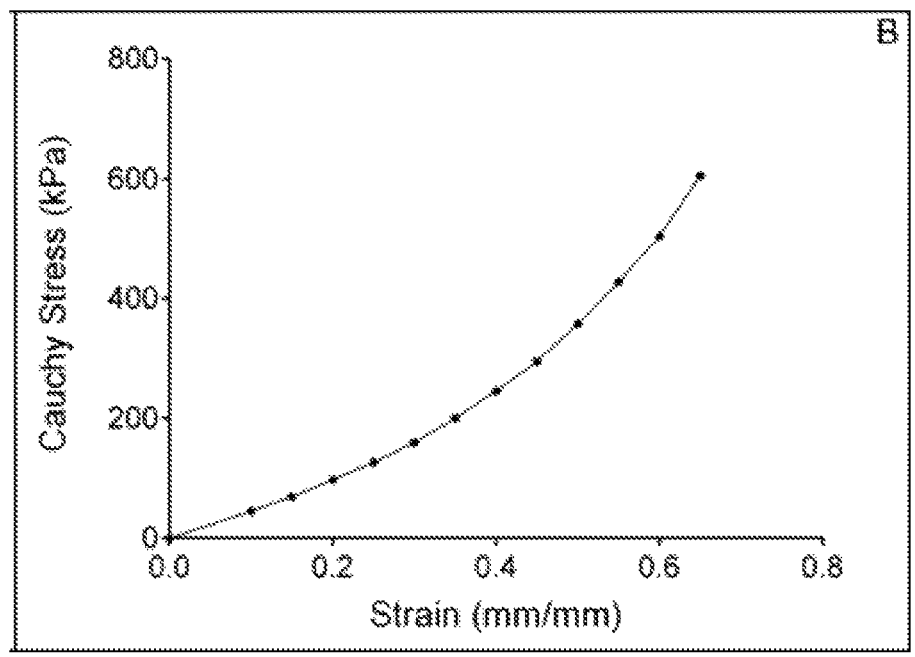
FIG. 11B is a graphical representation of the stress-strain response of PGS-PPF-Gd film.

Film Mechanical Tests. The PGS-PPF-Gd films were tested for mechanical strength. The films were attached individually to an INSTRON 5565 with a video extensometer to measure the axial displacement by noncontact. A 10 N load cell and pneumatic micro-grips were used to mount rectangular samples 12 mm×100 mm×0.7 mm (Instron, USA). An initial length of 50.4 mm at a pull rate of 2 mm/min was used. The stress and strain data were recorded and plotted for PGS-PPF, and are shown in FIG. 11A and for PGS-PPF-Gd in FIG. 11B.

Figure 12:
FIG. 12 is a fluoroscopic image depicting a PGS-PPF-Gd film inside a saline bag identified by white arrows.
Figure 13:
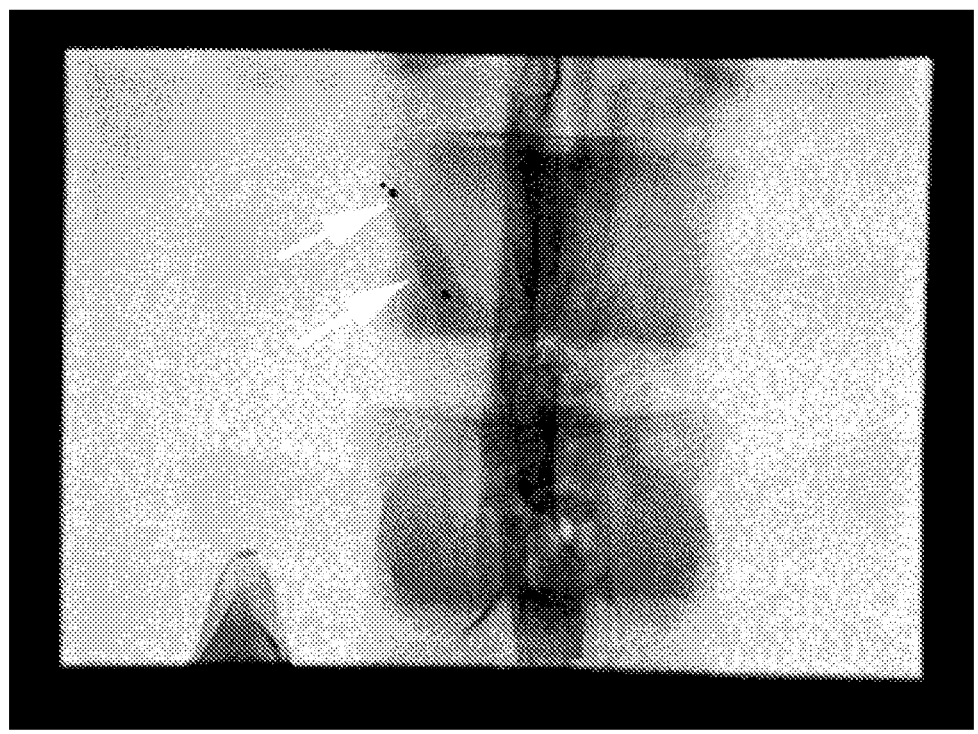
FIG. 13 is a fluoroscopic image depicting a PGS-PPF-Gd film wrapped around a stent on a practice spine identified by white arrows.

Fluoroscopic analysis. Fluoroscopic imaging on the PGS-PPF-Gd film was performed on a Toshiba Infinix I (Toshiba, America). The film was placed in a saline bag and imaged as show in FIG. 12. The film was also wrapped around a stent as shown in in FIG. 13. A platinum marker is on one end of the stent in FIG. 13 and the leads of the balloon are shown as well.

Figure 14:
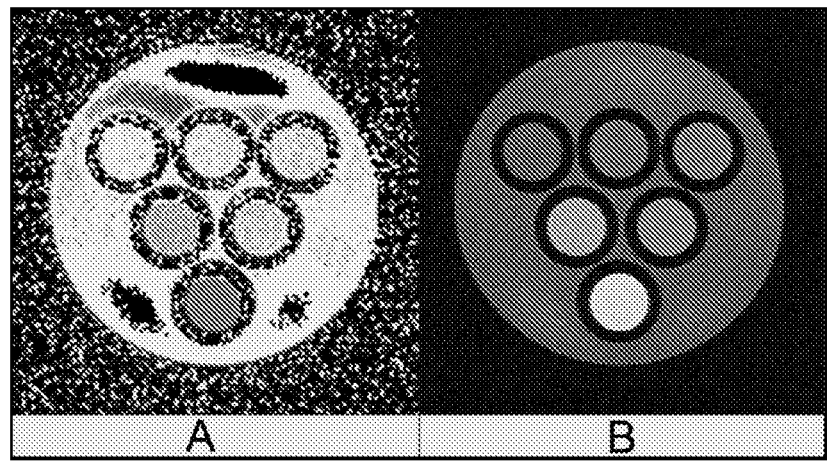
FIG. 14 is a $T_1$ weighted magnetic resonance image depicting phantom and reconstructed images of the six PPF-Gd samples of Table 2.
Figure 15:
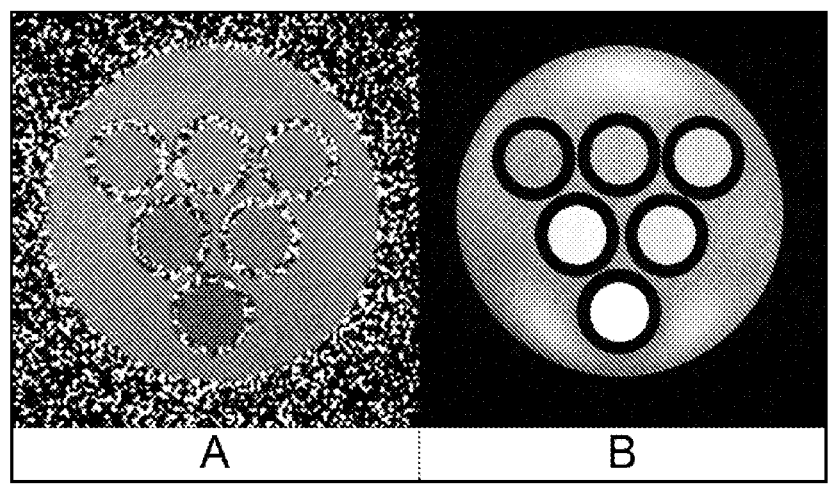
FIG. 15 is a $T_2$ weighted magnetic resonance image depicting phantom and reconstructed images of the six PPF-Gd samples of Table 2.
Figures 16A, 16B:
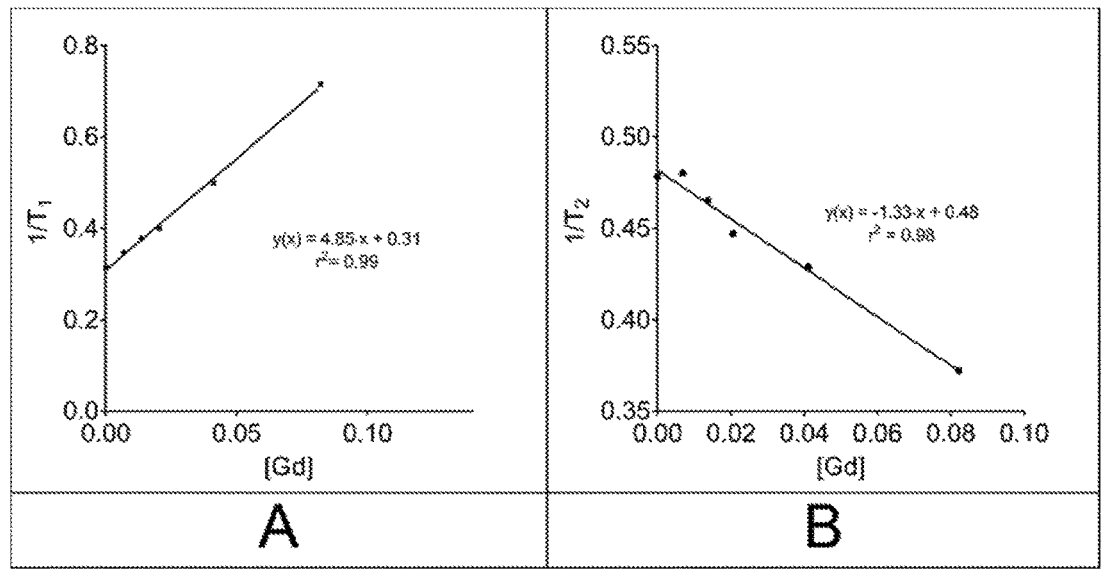
FIGS. 16A and 16B are a graphical representation of an experiment using linear regression to determine relaxivity coefficients ($r_1$ and $r_2$).

Magnetic resonance imaging (MM). PPF-Gd films were analyzed using MRI. MRI calibration was performed determining the T$_1$ and T$_2$ relaxation maps from vials containing six concentrations of PPF-Gd listed in Table 3. The MM machine generated phantoms of the vials and the image was reconstructed for concentration calibration as shown in FIGS. 14 and 15. The imaging data was than analyzed with ImageJ (U.S. National Institutes of Health, Bethesda, Md.) to determine the grey scale at each Gd concentration. Linear regression was performed with GraphPad Prism 6 (GraphPad Software, La Jolla, Calif.) to determine the relaxivity coefficients (r1 and r2). The relaxivity coefficients are r1=4.85 and r2=1.33 derived from FIGS. 16A and 16B.

TABLE 3

| Vial Number | Gd Concentration (mM) |
|---|---|
| 1 | 0.000 |
| 2 | 0.007 |
| 3 | 0.014 |
| 4 | 0.021 |
| 5 | 0.041 |
| 6 | 0.082 |

Example 5

Nanoparticle Blend, PLGA/PPF-Gd

Nanoparticles containing PLGA/PPF-GD and corticosteroid were prepared using a solvent displacement technique. PLGA-PPF-Gd (PLGA/PGFA) was synthesized as stated above. PLGA was dissolved in THF solvent followed by the addition of dexamethasone. An equal amount of prepolymer PPF-Gd was dissolved into the mixture followed by 5 mL of surfactant and sonication for 45 minutes. THF was removed via evaporation at room temperature and the collected nanoparticles were centrifuged and washed three times with distilled water at 1000 rpm.

Example 6

Characterization of Nanoparticles

Figure 17:
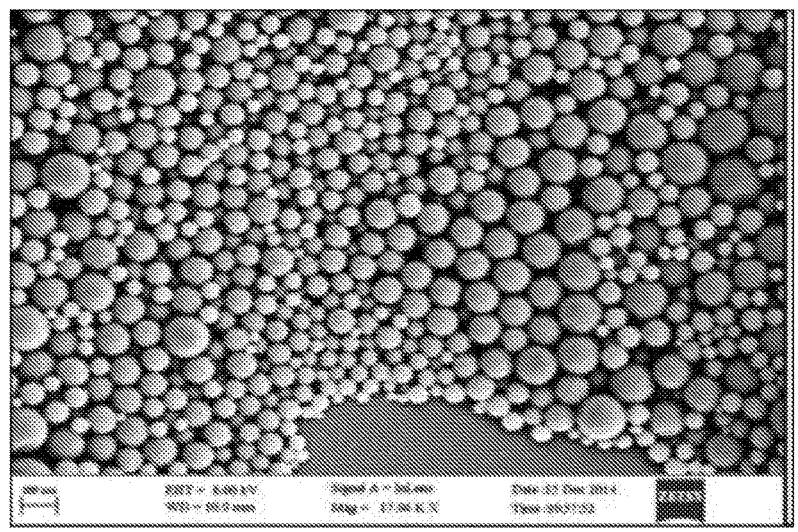
FIG. 17 is a Scanning Electron Microscopy image of nanoparticles of the present invention.

Scanning Electron Microscopy (SEM). The nanoparticles of Example 5 were characterized by SEM operating at 1-10 kV. A suspension of nanoparticles was pipetted onto a glass slip, dried, and then sputter coated for 60 seconds in an Anatech Hummer VI with gold/palladium as shown in FIG. 17. Effective hydrodynamic diameter and zeta potential were evaluated using Dynamic Light Scattering (DLS) (ZetaPALS, Brookhaven Instruments, Novata, Calif., USA).

Differential Scanning Calorimeter (DSC) analysis. The glass transition temperature, $T_g$, of the particles were determined by using a Q20 DSC with a temperature sweep from 10° C. to 150° C. The glass transition temperatures were reported after the second heating cycle and are listed in Table 4.

Example 7

Drug Efficiency and Cumulative Drug Release

Drug (dexamethasone (DEXA)) loading efficiency and cumulative drug release was determined by use of Dionex Ultimate 3000 High Pressure Liquid Chromatography and an Acclaim C30 column (Thermo Fisher Scientific). Dexamethasone release was determined via HPLC. DEXA-loaded nanoparticles (0.5 mL) suspended in distilled water (pH 7.38) was pipetted into MINI Dialysis Device (Slide-A-Lyzer 10K MWCO, Thermo Scientific USA). A dialysis device was inserted into a 2 mL tube filled with distilled water. The assembled dialysis apparatus was placed on a shaker in a 37° C. incubator (n=10 per group) and sealed. A portion (1 mL) the solution from tube was removed after 2, 4, and 7 days, and then weekly until end of the release experiment.

Figures 18A, 18B:
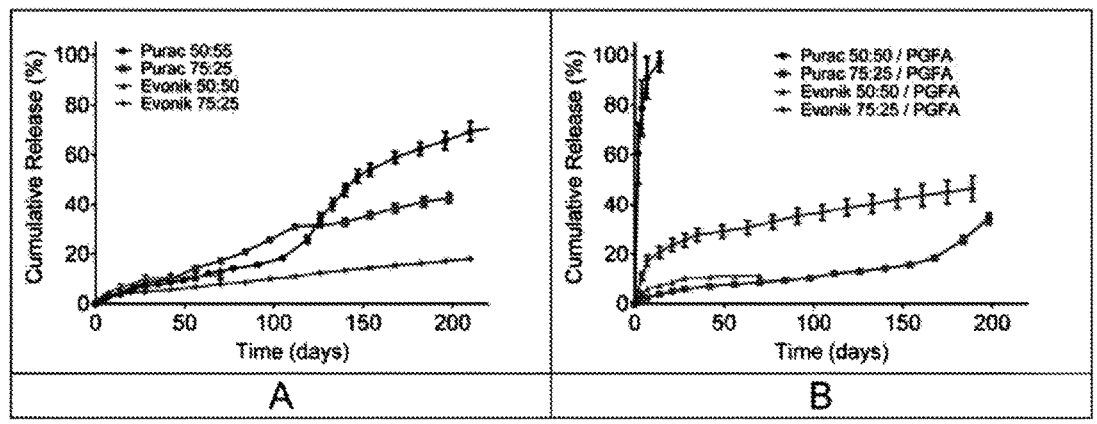
FIG. 18A is a graph of time in days versus cumulative release of various surfactants.
FIG. 18B is a graph of time in days versus cumulative release nanoparticles of the present invention that include a corticosteroid.

Two PLGA copolymer ratios (50:50 and 75:25) from commercial manufactures Corbion Purac® (USA) Evonik Resomer® (USA) were parameterized after blending with PGFA and compared to a PLGA control and are listed in Table 4. The addition of PGFA decreased the particle effective hydrodynamic diameter. All particles formulated with PLGA only, have mean effective diameters over one micron with some as large as 55 microns. All of the blended particles have mean effective diameters less than one micron with some as small as 480 nm. A similar trend was noted for zeta potential and $T_g$. The blending of PGFA decreased the magnitude of zeta potential and $T_g$ for all groups. Both zeta potential and $T_g$ are direct measurements of particle and polymer chain stability. The blending of PLGA and PGFA did increased drug loading efficiency for all polymer groups. Formulations with PLGA only, released dexamethasone more slowly than blend formulations. Overall, the copolymers from Corbion Purac® released faster than the copolymers from Evonik Resomer®. FIG. 18A is a graph of time in days versus cumulative release of various copolymers controls. FIG. 18B is a graph of time in days versus cumulative release nanoparticles of the present invention that includes a corticosteroid. Purac 50:50 group shows a biphasic release with an inflection point around 120 days. The Evonik 75:25 demonstrated the most predictable and controlled linear release throughout the experimental time frame. The Purac 50:50/PGFA blend showed an extreme shortening of drug release lifetime with 99% of dexamethasone released after two weeks. Purac 75:25/PGFA blend showed a biphasic release with an inflection point around 160 days. The cumulative release for Purac 75:25/PGFA blend was the lowest at the beginning of the experimental time frame and increased released was not observed until after day 100. Evonik 75:25/PGFA blend demonstrated a controlled increased release up to day 30 followed by a predictable linear release as shown in FIG. 18B.

TABLE 4

| Particle Group | Effective Diameter (μm) | Zeta Potential (mV) | DLE (%) | Tg (° C.) | Release Lifetime |
|---|---|---|---|---|---|
| PURAC 50:50 | 32.3 ± 4.4 | −24.3 ± 2.0 | 60.0 ± 2.3 | 50.0 ± 2.3 | 14 months (98%) |
| PURAC 50:50/PGFA | 0.75 ± 0.05 | −12.5 ± 3.5 | 57.2 ± 0.8 | 26.1 ± 0.3 | 2 weeks (99%) |
| PURAC 75:25 | 3.3 ± 0.4 | −9.4 ± 0.6 | 76.4 ± 2.4 | 49.8 ± 1.0 | 7 months (40%) |
| PURAC 75:25/PGFA | 0.48 ± 0.04 | −4.3 ± 1.3 | 97.6 ± 0.7 | 34.7 ± 1.1 | 6 months (92%) |
| EVONIK 50:50 | 2.6 ± 0.4 | −50.1 ± 1.1 | 78.0 ± 1.6 | 45.6 ± 1.2 | 3 months (12%) |
| EVONIK 50:50/PGFA | 0.78 ± 0.03 | −4.3 ± 1.3 | 97.4 ± 1.2 | 24.6 ± 2.8 | 3 months (12%) |
| EVONIK 75:25 | 54.9 ± 7.5 | −20.8 ± 3.0 | 65.2 ± 1.5 | 50.0 ± 0.3 | 7 months (18%) |
| EVONIK 75:25/PGFA | 0.69 ± 0.04 | −7.8 ± 1.1 | 81.8 ± 3.7 | 43.5 ± 1.1 | 8 months (50%) |

Example 8

In-Vitro Biocompatibility of Polymeric Theranostic Nanoparticles (PTNPs)

Colorimetric XTT assay. The viability of cells was evaluated using a colorimetric XTT assay using Human Dermal Fibroblasts Cells (HDF) and Human Tracheal Epithelial Cells (TEC). The fundamentals of the assay were based on the ability of metabolically active cells to reduce the XTT tetrazolium salt, which caused a colorimetric change of formazan. Using a 96-well plate and a cell inoculation time of 48 hrs, 50 µL of XTT labeling mixture was pipetted into each well and the microplate was incubated for 5 h. A microplate reader (Synergy HT, BIOTEK, Winooski, Vt., USA) with a specific absorbance filter of 475 nm and non-specific absorbance filter of 660 nm was used to measure the absorbance of each well. The fraction of viable cells in the experimental groups was normalized according to control viability equal to 100%.

Figure 19:
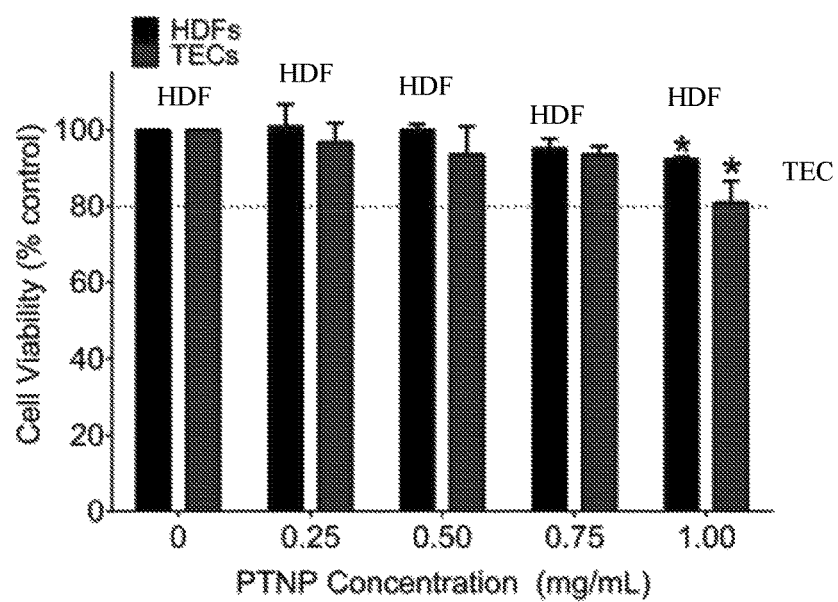
FIG. 19 is a graph of polymeric theranostic nanoparticles (PTNP) of the present invention concentration in mg/mL versus cell viability in percent control.

XTT cell viability assay. Biocompatibility of Evoink 75:25 PLGA/PGFA PTNPs was evaluated using a XTT cell viability assay and confirmed using fluorescent microscopy using live/dead staining. With a 24 h incubation, PTNP concentrations lower than 0.75 mg/mL had no cytotoxic effect observed in human dermal fibroblasts (HDFs) or tracheal epithelial cells (TECs) compared to the control (See, FIG. 19). In FIG. 19, graph bars representing HDFs the right of the graphical bars representing TECs in each grouping.

Figure 20:
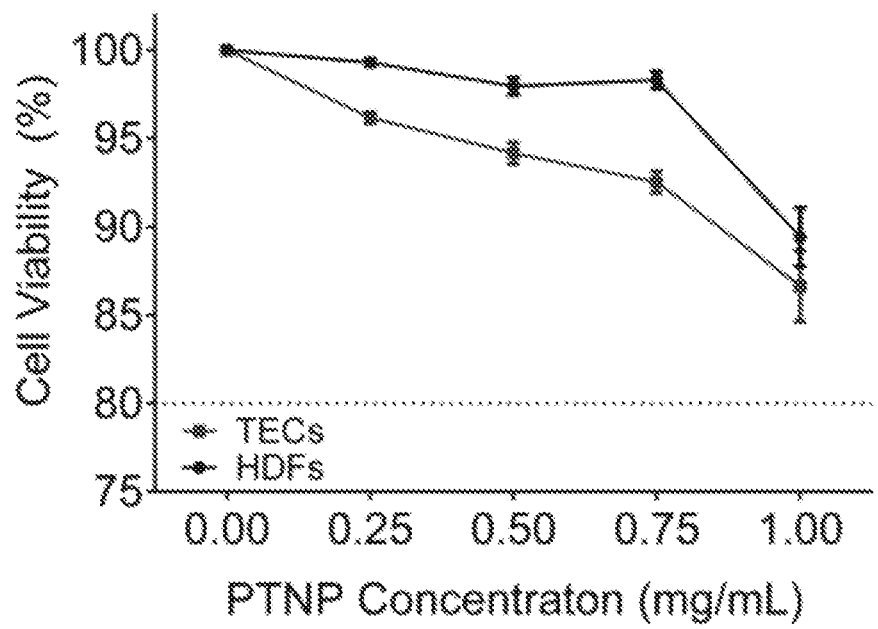
FIG. 20 is graph of PTNP of the present invention in mg/mL versus cell viability in percent (TECs (top line) and HDFs (bottom line)

Live/Dead Viability/Cytotoxicity Kit assay. The viability of cells was also evaluated using a Live/Dead Viability/Cytotoxicity Kit (Life Technologies, Carlsbad, Calif., USA). Calcein AM was diluted with PBS to a final concentration of 2 µM and ethidium homodimer-1 to 4 µM. Samples were analyzed via fluorescent microscopy (EVOS® FL Auto with Onstage Incubator, Life Technologies, Grand Island, N.Y., USA) equipped with FITC filter for calcein and TRITC filter for ethyl-D. Cells were counted per condition with green fluorescent indicating live cells and red fluorescence indicate dead cells. Cell images were counted using NIS-Elements Basic Research Software (Nikon Instruments Inc., Melville, N.Y., USA). Each cell type exhibited normal cell morphology with very few dead cells in any of the experimental concentrations. HDFs showed significant spreading in the presence of PTNPs and higher cells counts than the respective control at each concentration except at 1.00 mg/mL. The dead cell count in HDF images was not significantly different from the control for all experimental groups except at 1.00 mg/mL. TECs also showed an increase in cell count at 0.25 mg/mL compared to its control though a decrease in cell count as concentration increased was observed at 0.50 mg/mL or higher. The number of dead cells in TEC images was not significantly different in each experimental concentration as shown in FIG. 20.

Example 9

Therapeutic Effect of PTNPs of the Present Invention

Figure 21:
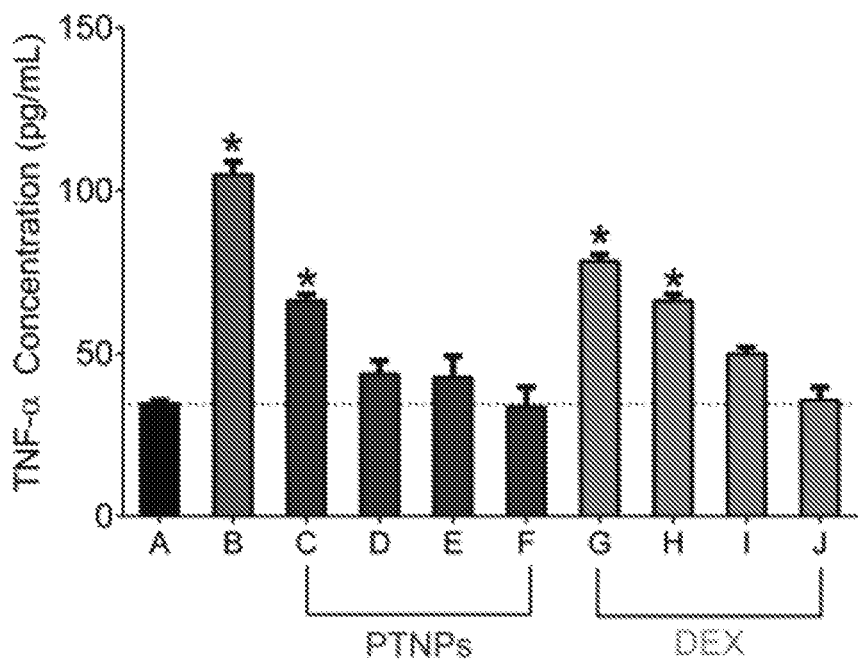
FIG. 21 shows graphs of controls, PTNPs of the present invention with a corticosteroid and the corticosteroid (dexamethasone) versus TNF-α concentration (pg/mL).
Figure 22:
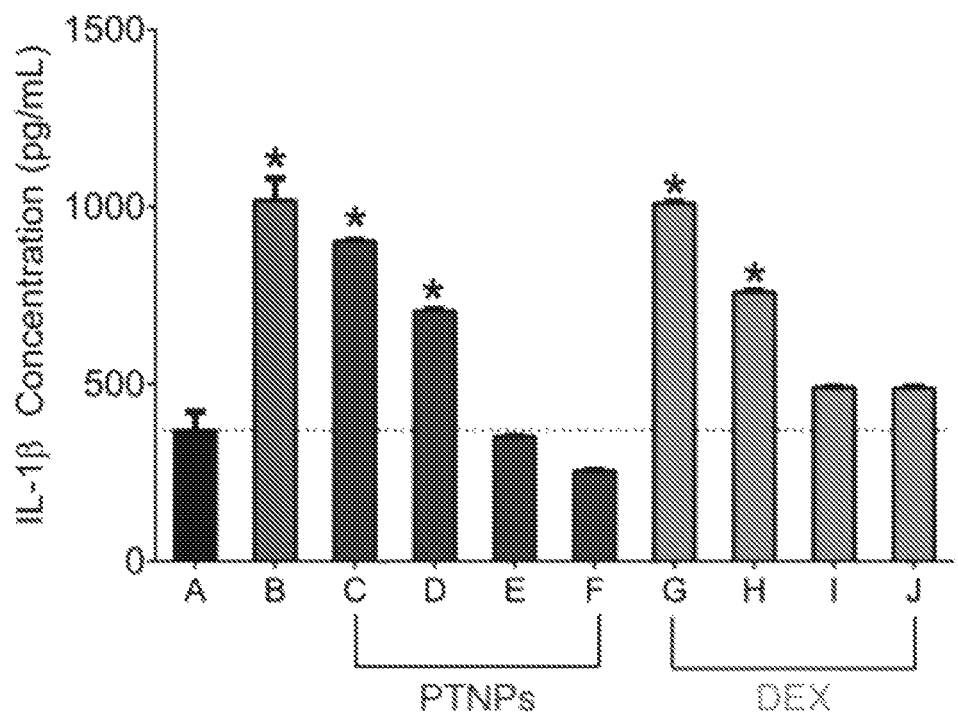
FIG. 22 shows graphs of controls, PTNPs of the present invention with a corticosteroid and the corticosteroid (dexamethasone) versus IL-1β concentration (pg/mL).

Therapeutic effect. The anti-inflammatory effect of dexamethasone loaded PTNPs after 24 h exposure versus TNF-α, and IL-1β concentrations were measured in RAW 264.7 cells and are depicted in FIGS. 21 and 22. Table 5 lists the results and experimental group assignments for the experiment. PTNP concentrations were compared to free dexamethasone in media, which simulates systemic delivery. The experimental design included the expected concentrations of dexamethasone released from PTNP groups. Compared to the control (no treatment or LPS, Group A) a significant increase in TNF-α and IL-1β was observed with Lipopolysaccharide (LPS) stimulation, Group B. TNF-α concentrations of mouse macrophages exposed to PTNPs at a concentration of 0.50-1.00 mg/mL were not significantly different from the control (FIG. 21 Group D-F). A concentration of 0.25 mg/mL significantly lowered TNF-α concentration compared to LPS stimulated but not enough to be comparable to the control (FIG. 21 Group C). Groups with free dexamethasone in media at a concentration of 1 and 2 mg/mL also lowered TNF-α concentrations to control levels (FIG. 21 Groups I&J). Free dexamethasone concentrations of 0.10-0.50 mg/mL also lowered TNF-α but not enough to be comparable to the control. Similar results were observed with IL-1β ELISA with the exception that a PTNP concentration of at least 0.75 mg/mL was required to reduce IL-1β concentration to control levels (FIG. 22). The ELISAs demonstrated that a concentration of 0.23 mg/mL of dexamethasone or a PTNP concentration of 0.75 mg/mL was required to maintain TNF-α and IL-1β control concentration levels in the presence of stimuli.

TABLE 5

| | Treatment | | | Cytokine | |
| | | | DEX | Concentration | |
| Group | PTNPs (mg/mL) | Free DEX (mg/mL) | Concentration (mg/mL) | TNF-α (pg/mL) | IL-1β (pg/mL) |
|---|---|---|---|---|---|
| A | — | — | 0.00 | 35 ± 1 | 369 ± 52 |
| B | — | — | 0.00 | 104 ± 6 | 1018 ± 61 |
| C | 0.25 | | 0.07 | 66 ± 3 | 903 ± 4 |
| D | 0.50 | | 0.15 | 43 ± 6 | 707 ± 7 |
| E | 0.75 | | 0.23 | 42 ± 13 | 352 ± 2 |
| F | 1.00 | | 0.31 | 33 ± 9 | 256 ± 2 |
| G | | 0.10 | 0.10 | 78 ± 3 | 1009 ± 7 |
| H | | 0.50 | 0.50 | 66 ± 3 | 759 ± 7 |
| I | | 1.00 | 1.00 | 50 ± 3 | 491 ± 2 |
| J | | 2.00 | 2.00 | 35 ± 6 | 489 ± 4 |

Example 10

PCFA, PGCFA Drug Release

Figure 23:
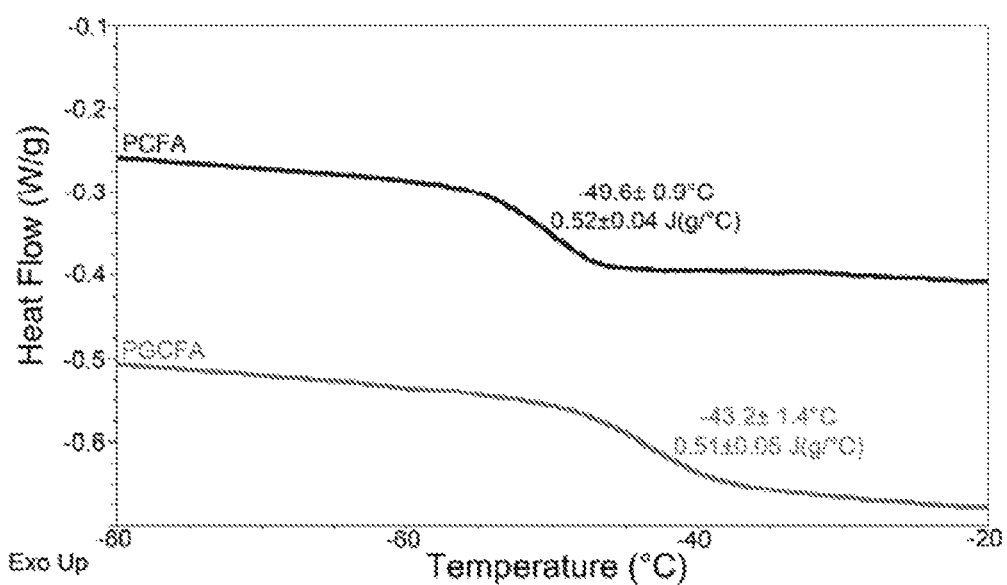
FIG. 23 depicts Differential Scanning calorimetry (DSC) graphs of PGCFA and PCFA of the present invention.

PCFA and PGCFA was synthesized as stated above and characterized by polymer molecular weight, degradation kinetics, polymer rheology, drug release, and bacterial assay. Polymer molecular weight and degradation kinetics were determined via Gel Permeation Chromatography (GPC)/Refractive Index Detection (RI). 5 mg of polymer was dissolved in tetrahydrofuran (THF) and analyzed using Ultimate 300 High Pressure Liquid Chromatography (HPLC) system (Thermo Scientific Dionex, Chicago, Ill., USA) and RI detector (VE3580 Malvern, Houston, Tex., USA) with the I-OLIGO column (Viscotek, 10 µm, 7.8×30 cm). The mobile phase was 100% THF with a flow rate of 1.0 mL/min. An injection volume of 30 µL was used with the column oven set to 35° C. Collected data was analyzed with OmniSec 4.7 software (Malvern, Houston, Tex., USA). Polystyrene standards were used for molecular weight calibration. The polymer molecular weight for prepolymer PPF, PCFA and PGCFA was 612 Da, 1360 Da, and 1376 Da respectively. Polymer thermal properties were determined using Differential Scanning calorimetry (DSC). Approximately 5 mg of polymer pipetted into a TZero aluminum pan, sealed, and analyzed on a Q20 differential scanning calorimeter (TA Instruments, New Castle, Del., USA). Samples were equilibrated at −100° C., and ramped to 75° C. at a rate of 10° C./min and then held isothermal for one minute. The sample was then cooled to −100° C. at a rate of 50° C./min. Samples were thermally cycled two times and data was reported on the second heating cycle. Heat curves were analyzed on TA Universal Analysis Software (TA Instruments, New Castle, Del., USA). The prepolymer PPF, PCFA, and PGCFA have glass transition temperatures of −38.5±0.5° C., −49.6±0.9° C., and −43.2±1.4° C. respectively (See, FIG. 23).

Figures 24A, 24B, 24C:
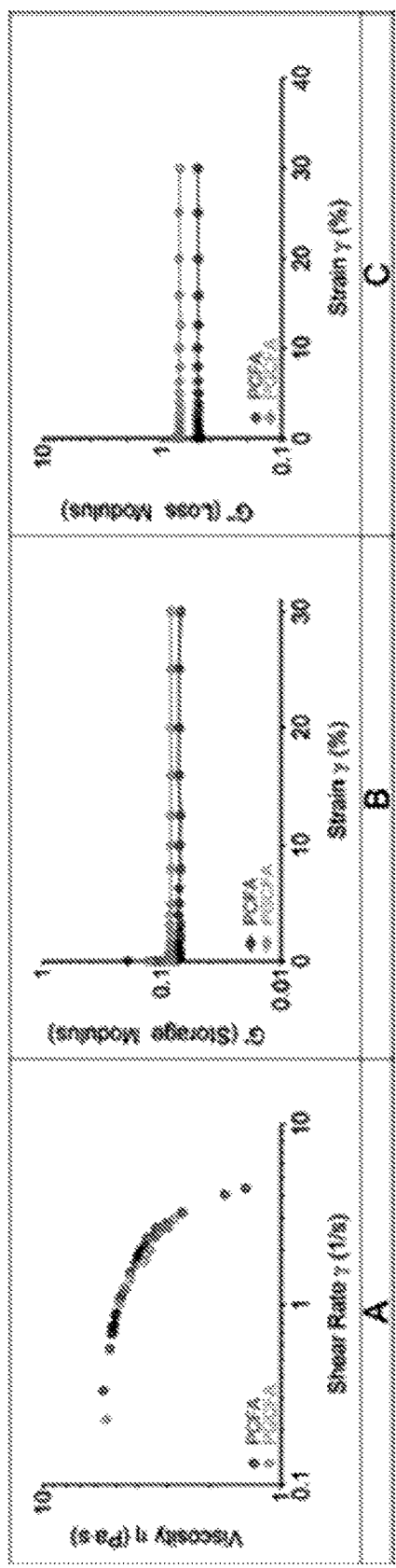
FIGS. 24A-C are rheological characterization of PCFA and PGCFA at 37° C. Assessment of polymer viscosity using a broad torque range of 0.1-1000 µN·m (FIG. 24A). Assessment of storage modulus (G') (FIG. 24B) and loss modulus (G") using a strain range of 0.1-30% (FIG. 24C).

Viscoelastic behavior of polymers was determined via AR G2 rheometer (TA Instruments, New Castle, Del., USA). For all polymers, a gap size of 1000 μm was used. Polymers were analyzed at 37° C. with data recording at 10 points per decade. Viscosity (η) was analyzed at a constant frequency (ω) of 1 rad/s and a broad torque range of 0.1-1000 μN/m respectively. Shear storage modulus (G') and shear loss modulus (G") were analyzed at a constant frequency (ω) of 1 rad/s and a strain (γ) range of 0.1-30%. All of these polymers exhibit Non-Newtonian pseudoplastic behavior with viscosity of the material being dependent on the shear rate with shear thinning occurring as shown in FIG. 24 and no yield stress of the polymer.

Figure 25:
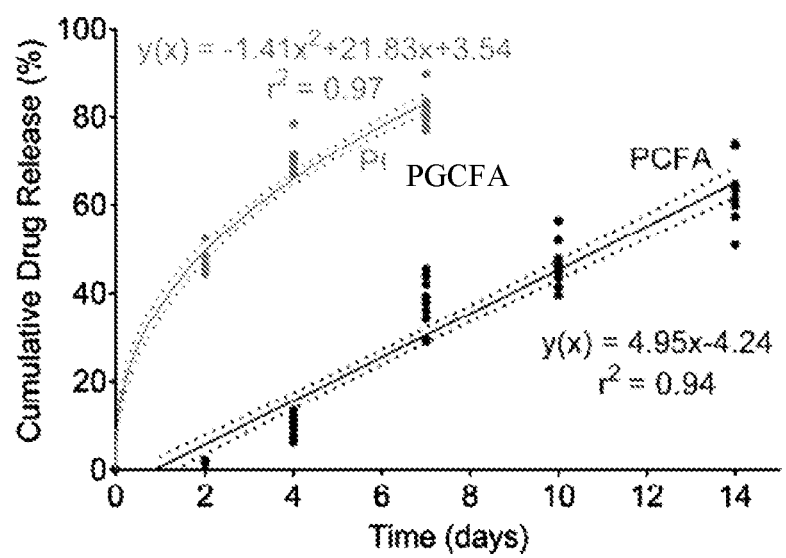
FIG. 25 are graphs of cumulative release of ciprofloxacin at 37° C. in aqueous environment for PGCFA (top line) and FCFA (bottom line)
Figure 26:
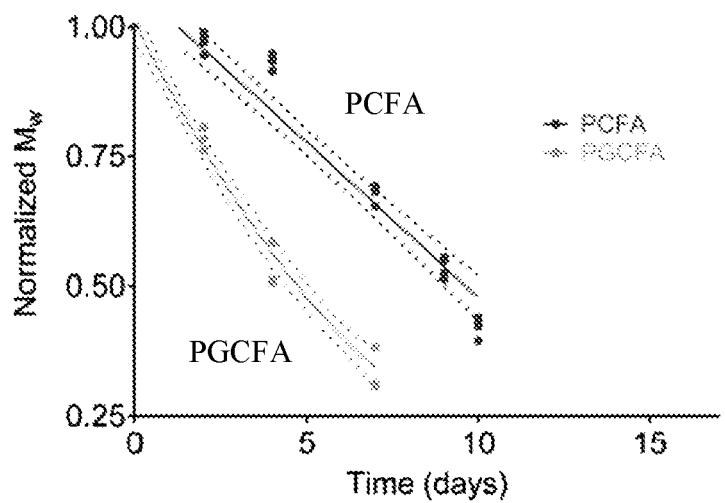
FIG. 26 are graphs of degradation kinetics of PCFA (top line) and PGCFA (bottom lines) in deionized water at 37° C.

Cumulative ciprofloxacin release was determined using HPLC. 0.5 g of polymer was measured into a 2 mL vial and immersed in distilled water (pH 7.4). Vials were placed in a shaker over operating at 37° C. and 120 rpm. Distilled water was removed from vials at days 2, 4, 7, 10, and 14 days. Samples were analyzed via an Acclaim C30 column (Thermo Fisher Scientific, 3 μm, 3.0×15 mm) with a mobile phase of acetonitrile, water, and trifluoroacidic acid. A flow rate of 0.5 mL/min with an injection volume of 25 μL was used with UV diode array set at 240 nm. FIG. 25 shows the cumulative release of ciprofloxacin from PCFA and PGCFA follow the same mathematic model that mirrored the polymer degradation shown in FIG. 26. Cumulative release of ciprofloxacin best fit a zero order release model for PCFA while a second order model best fits for PGCFA release.

Bacterial strains were grown on Mueller-Hinton agar (Sigma Aldrich) following manufacturer protocol and National Committee of Clinical Laboratory Standards (NCCLS). *Escherichia coli* (124300), *Klebsiella pneumoniae* (155095A), *Moraxella catarrhalis* (154928), and *Pseudomonas aeruginosa* (155250A) were all obtained from Carolina® (Carolina Biological Supply Company, Burlington, N.C., USA). A standard curve was developed for each bacterial strain using published minimum inhibitory concentration (MIC) values. A stock solution of 10 mg/μL ciprofloxacin in deionized water was made and diluted at least five times to create a standard set for each bacterial strain (Table 6).

TABLE 6

| Bacterial Strain | Concentration Standards (ng/μL) | | | | | | |
| --- | --- | --- | --- | --- | --- | --- | --- |
| | 1 | 2 | 3 | 4 | 5 | 6 | 7 |
| E. coli | 0 | 1.25 | 2.5 | 5 | 10 | 20 | 40 |
| K. pneumoniae | 0 | 1 | 10 | 15 | 20 | | |
| M. catarrhalis | 0 | 5 | 10 | 20 | 40 | 80 | |
| P. aeruginosa | 0 | 50 | 150 | 300 | 600 | 1000 | |

Figure 27:
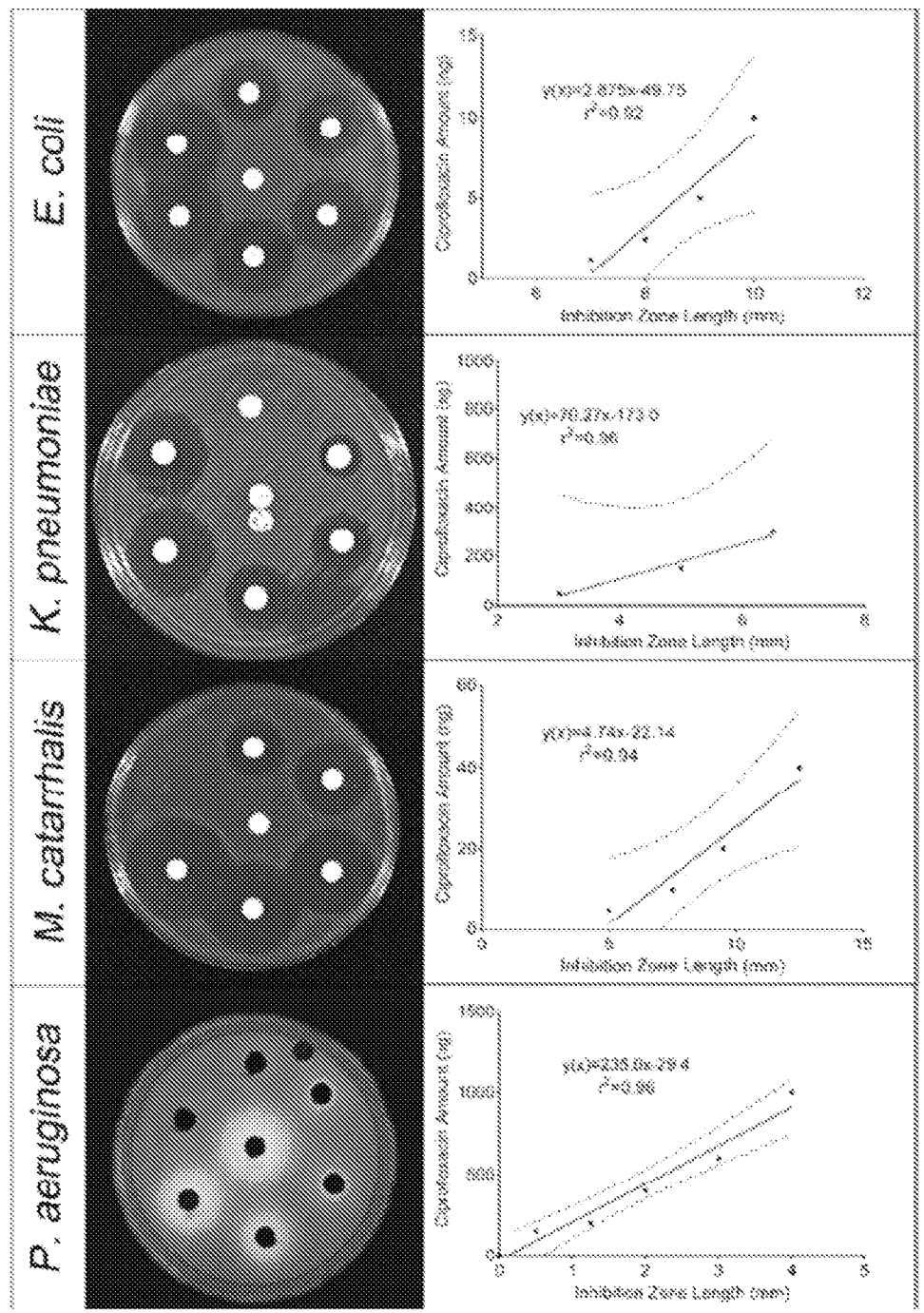
FIG. 27 are images and linear regression analysis of Kirby-Bauer disk diffusion standards of the four airway bacteria strains. Images (Left) of typical incubated standard plate for each strain with corresponding linear regression analysis (Right) with 95% confidence interval of ciprofloxacin amount based on measured inhibition zone length (n=3 per group).
Figures 28A, 28B, 28C, 28D:
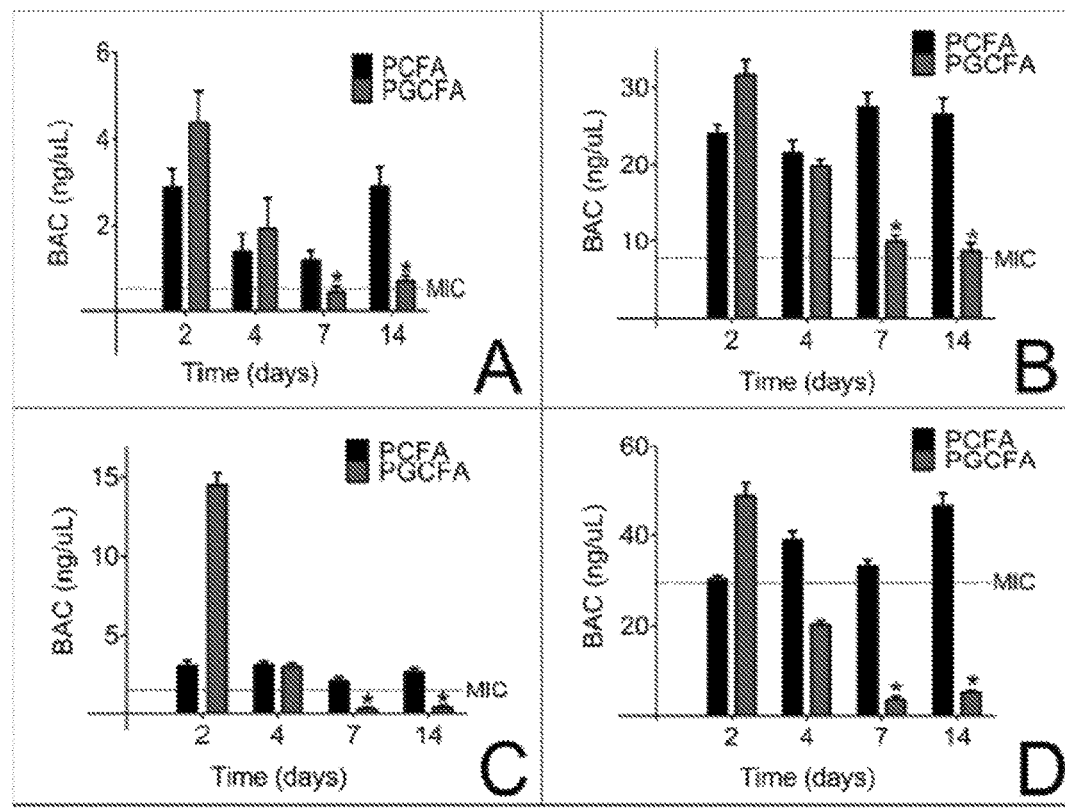
FIGS. 28A-28D are graphs of measured biologically active concentrations (BACs) of ciprofloxacin for 14 days from sensitivity assays. The dotted line indicated minimum inhibitory concentration (MIC) for each strain. *Escherichia coli* BAC with MIC of 2 ng/µl (FIG. 28A). *Klebsiella pneumoniae* BAC with MIC 8 ng/µl (FIG. 28B). *Moraxella catarrhalis* BAC with MIC 2 ng/µl (FIG. 28C). *Pseudomonas aeruginosa* BAC with MIC of 30 ng/µl (FIG. 28D). Statistical significance of student T-test (p<0.05) noted with asterisk. Data shown mean±SEM, n=9 per group. Graphical bars representing PCFA are to the left of the PGCFA graphical bars in each grouping.

A standard diffusion assay protocol was used as prior description with the following modifications (22). 20 μL of each standard was pipette onto a blank sterile sensitivity disk and dried for one hour. Bacterial isolate from a single colony was vortexed in 1 mL of Luria broth (LB). A sterile cotton swab was dipped into the LB and the surface of the agar plate was inoculated. Using forceps, dried disks were spaced evenly apart from one another and gently pressed to ensure adherence. Plates were inverted and incubated for 24 hr at 37° C. Plates were then imaged with BioRad Chemidoc™ MP Imaging System (BioRad, Hercules, Calif., USA). Inhibition zone length was determined using ImageJ (Rasband, W. S., ImageJ, U.S. National Institutes of Health, Bethesda, Md., USA, http:/imagej.nih.gov/ij/1997-2015). Inhibition zone length was measured from edge of sensitivity disk to edge of no growth (n=4 per disk). Linear regression analysis was then performed to determine biologically active concentration (BAC) using GraphPad Prism 6 (GraphPad Software, La Jolla, Calif., USA). Following the same method as ciprofloxacin release kinetics, deionized water solutions from degrading polymers were removed to simulate in-vivo polymer degradation and release. PCFA and PGCFA were compared with prepolymer PPF (that contains no ciprofloxacin) as a control. Ciprofloxacin concentration was determined in each sample using HPLC. Each degradation time point had a separate plate for each bacterial strain. A known volume of the degradation product solution was pipetted onto a blank sterile sensitivity disk. The selection of the volume of degradation product for a particular strain was based on polymer degradation kinetics and indexed to match the experimentally determined ciprofloxacin MIC for each respective strain (Table 7). Plates were incubated for 24 hr and inhibition zone lengths were determined as described above. BAC was then determined at each time point for each bacterial strain using linear regression equation from standards. All experimental plates with degradation extracts from PCFA and PGCFA showed the formations of growth inhibition zones in FIG. 27. All bacteria except *M. catarrhalis* showed no inhibition zone formation with prepolymer PPF degradation extracts. *M. catarrhalis* unlike the other strains is gram-negative. The susceptibility of *M. catarrhalis* is increased to prepolymer PPF due to the difference in membrane permeability comparative to gram-positive strains. The formation of inhibition zones indicated that synthesis conditions and subsequent degradation did not denature the antibacterial properties of ciprofloxacin in FIG. 25. All measured BAC values from PCFA were within the known MIC range for the full testing period. For all bacteria except *P. aeruginosa*, BAC values from PGCFA were above the MIC until Day 4 then fell below the lower limit as shown in FIGS. 28A-D. Plates with PGCFA degradation extracts exhibited large inhibition zones at day 2 and 4 and tapered by day 7. PCFA showed a relatively consistent inhibition zone length for each respective volume throughout the two weeks.

TABLE 7

| Bacterial Strain | Volume of Solution (μL) | | | | |
| --- | --- | --- | --- | --- | --- |
| | 1 | 2 | 3 | 4 | 5 |
| Escherichia coli | 0 | 1 | 2 | 5 | 10 |
| Klebsiella pneumoniae | 0 | 1 | 10 | 15 | 20 |
| Moraxella catarrhalis | 0 | 1 | 2 | 5 | 10 |
| Pseudomonas aeruginosa | 0 | 15 | 20 | 30 | 35 |

The invention claimed is:
1. A compound having a general structure of (I):

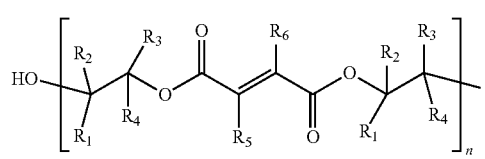

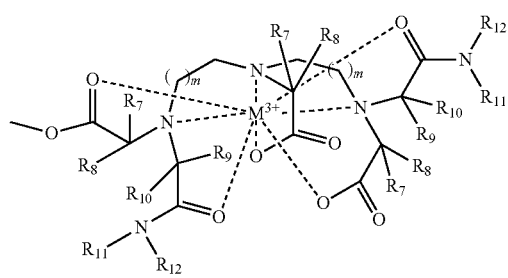

wherein $R_1$, $R_2$, $R_3$, $R_4$, $R_5$, $R_6$, $R_7$, $R_8$, $R_9$, $R_{10}$, and $R_{11}$ are each, individually, a hydrogen atom or an alkyl group;
n is 1 to 4, preferably 2;
m is 0 through 5, preferably 1; and
M is a transition, lanthanide, or actinide ion.

2. The compound of claim 1, wherein $R_1$ and $R_{11}$ are methyl, and $R_2$, $R_3$, $R_4$, $R_5$, $R_6$, $R_7$, $R_8$, $R_9$, $R_{10}$, and $R_{12}$ are hydrogen.

3. The compound of claim 1, wherein m is 1.

4. The compound of claim 1, wherein M is gadolinium.

5. The compound of claim 1, comprising a monomer where n is 1.

6. The compound of claim 1, wherein the compound is bioresorbable.

7. The compound of claim 1, wherein the compound emits fluorescent X-rays under electromagnetic radiation, emits electromagnetic radiation waves under an oscillating magnetic field, or both.

8. The compound of claim 1, wherein the compound is a film.

9. The compound of claim 1, wherein the compound is:

10. A method to prepare the compound of claim 1, the method comprising:

(a) obtaining a dialkyl alkylenedioic acid, a 1,2-diol, anhydrous gadodiamide, and a Lewis acid catalyst or Lewis base catalyst; and (b) reacting the dialkyl alkylenedioic acid, the 1,2-diol, gadodiamide and the Lewis acid catalyst or Lewis base catalyst under conditions sufficient to produce the polymer.

11. The method of claim 10, wherein the dialkyl alkylenedioic acid and the 1,2-diol of are diethyl fumarate and propylene glycol.

12. The method of claim 10, wherein the Lewis acid is zinc chloride or the Lewis base is ciprofloxacin.

13. The method of claim 10, wherein the conditions comprise a temperature of 150° C. to 200° C., preferably 170° C. to 190° C., most preferably 180° C., a pressure of 1 to 5 mmHg, preferably 1 to 2 mmHg, most preferably 1 mmHg with vigorous agitation.

14. The method of claim 13, wherein the vigorous agitation comprises stirring at 200 to 300 rpm, 210 to 300 rpm, or 220 rpm.

15. The method of claim 10, wherein a molar ratio of Lewis acid or Lewis base to dialkyl alkylenedioic acid is 0.0004:1 to 0.06:1, preferably 0.02:1.

16. The method of claim 10, wherein a molar ratio of dialkyl alkylenedioic acid to 1,2-diol is 1:2 to 1:5, preferably 1:3.

17. The method of claim 10, wherein a molar ratio of gadodiamide to dialkyl alkylenedioic acid is 0.003:1 to 0.06:1, preferably 0.02:1.

18. The method of claim 10, wherein the conditions further comprise terminating the reaction when the molecular weight of the polymer is 500 Da to 1500 Da, preferably about 1000 Da.

* * * * *

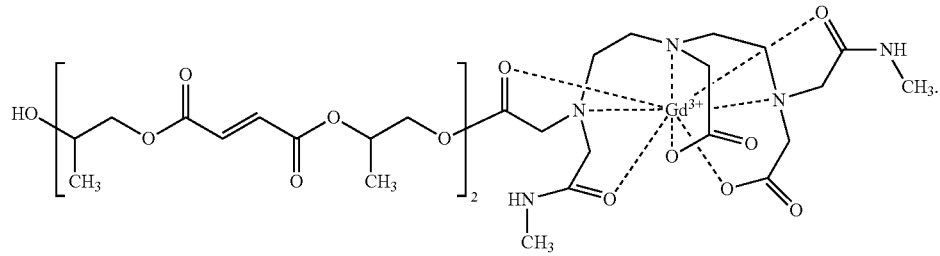

UNITED STATES PATENT AND TRADEMARK OFFICE
CERTIFICATE OF CORRECTION

PATENT NO. : 10,501,575 B2
APPLICATION NO. : 15/573892
DATED : December 10, 2019
INVENTOR(S) : Welch et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this
Eleventh Day of August, 2020

Andrei Iancu
*Director of the United States Patent and Trademark Office*